US010648901B2

(12) United States Patent
Scipolo et al.

(10) Patent No.: US 10,648,901 B2
(45) Date of Patent: May 12, 2020

(54) SYSTEM AND METHOD FOR ANALYZING DUSTY INDUSTRIAL OFF-GAS CHEMISTRY

(71) Applicant: TENOVA GOODFELLOW INC., Mississauga (CA)

(72) Inventors: Vittorio Scipolo, Mississauga (CA); Douglas J. Zuliani, Stittsville (CA); Avishekh Pal, Toronto (CA); Ovidiu Negru, Richmond Hill (CA)

(*) Notice: Subject to any disclaimer, the term of this patent is extended or adjusted under 35 U.S.C. 154(b) by 25 days.

(21) Appl. No.: 16/178,625

(22) Filed: Nov. 2, 2018

(65) Prior Publication Data

US 2019/0226980 A1 Jul. 25, 2019

Related U.S. Application Data

(63) Continuation of application No. 15/502,615, filed as application No. PCT/CA2015/000463 on Aug. 14, 2015, now Pat. No. 10,161,851.

(Continued)

(51) Int. Cl.
*G01N 21/03* (2006.01)
*G01N 21/39* (2006.01)
(Continued)

(52) U.S. Cl.
CPC ............ *G01N 21/03* (2013.01); *G01N 21/05* (2013.01); *G01N 21/39* (2013.01); *G01N 33/004* (2013.01);
(Continued)

(58) Field of Classification Search
CPC ........ G01N 21/05; G01N 21/03; G01N 21/39; G01N 21/253; G01N 33/005;
(Continued)

(56) References Cited

U.S. PATENT DOCUMENTS 4,746,218 A * 5/1988 Lord, III ............ G01N 21/3518
250/338.5
4,797,000 A 1/1989 Curtis
(Continued)

FOREIGN PATENT DOCUMENTS

DE 196 01 873 A1 8/1996
EP 1 876 439 1/2008
(Continued)

OTHER PUBLICATIONS

Electric and automation for electric arc furnace . . . Brochure [online], Siemens AG, brochure printed in Austra, 2012 . . . [Nov. 22, 2015] retrieved from the Internet:<URL:https://www.industry.siemens.com/datapool/industrysolutions/metals/simetal/en/electrics-and-automation-for-electric-arc-furance-en.pdf> (6 pages).

(Continued)

*Primary Examiner* — Sang H Nguyen

(57) ABSTRACT

An off-gas analyzer for analyzing $H_2O$ vapor, CO, $O_2$, $CO_2$ and/or $H_2$ in a furnace gas stream is fluidically coupled to a gas extraction probe. The analyzer includes an optical measurement cell having multiple sampling chambers, optically coupled to a laser. The analyzer measuring cell is housed within a heated cabinet having a heater operable to heat the interior thereof so as to maintain the extracted gas sample therein at a temperature about the condensation point of water. The analyzer allows for the analysis of the gas water vapour of wet off-gas samples.

20 Claims, 8 Drawing Sheets

Related U.S. Application Data

(60) Provisional application No. 62/037,821, filed on Aug. 15, 2014.

(51) Int. Cl.
*G01N 33/00* (2006.01)
*G01N 21/05* (2006.01)
*G01N 21/25* (2006.01)

(52) U.S. Cl.
CPC ......... *G01N 33/005* (2013.01); *G01N 21/253* (2013.01); *G01N 2021/399* (2013.01); *Y02A 50/243* (2018.01); *Y02A 50/244* (2018.01)

(58) Field of Classification Search
CPC ........... G01N 33/004; G01N 2021/399; Y02A 50/244; Y02A 50/243
See application file for complete search history.

(56) References Cited

U.S. PATENT DOCUMENTS

| | | | |
|---|---|---|---|
| 4,929,078 A | 5/1990 | Harmon | |
| 4,931,660 A | 6/1990 | Mayer | |
| 5,153,671 A | 10/1992 | Miles | |
| 5,222,389 A | 6/1993 | Wong | |
| 5,332,901 A | 7/1994 | Eckles | |
| 5,585,636 A | 12/1996 | Dollansky | |
| 5,773,828 A | 6/1998 | Akiyama | |
| 5,807,750 A * | 9/1998 | Baum | G01N 21/31 250/341.1 |
| 5,872,622 A | 2/1999 | Schildmeyer | |
| 6,369,387 B1 | 4/2002 | Eckles | |
| 6,429,935 B1 | 8/2002 | Duan | |
| 6,777,228 B2 | 8/2004 | Lejeune | |
| 7,022,922 B2 | 4/2006 | Nowakowski | |
| 7,180,595 B2 | 2/2007 | Willing | |
| 7,223,978 B2 | 5/2007 | Vuillermoz | |
| 2003/0160174 A1 | 8/2003 | Grant | |
| 2006/0144126 A1* | 7/2006 | O'Brien | G01N 1/2202 73/23.42 |
| 2007/0246653 A1 | 10/2007 | Zhou | |
| 2007/0291255 A1 | 12/2007 | Larsen | |
| 2009/0122380 A1 | 5/2009 | Dong | |
| 2010/0027013 A1* | 2/2010 | Hansen | G01N 21/4738 356/432 |
| 2015/0377750 A1* | 12/2015 | Scipolo | G01N 1/2205 73/29.01 |

FOREIGN PATENT DOCUMENTS

| | | |
|---|---|---|
| WO | WO 95/16904 | 6/1995 |
| WO | WO 2012/126471 | 9/2012 |

OTHER PUBLICATIONS

Product catalog [online], Fuji Electric Co., catalog printed in Japan, 2013 [retrieved on Nov. 23, 2015]. Retrieved from the Internet: <URL: http://www.americas.fujielectric.com/sits/default/files/21C2-E-0005.pdf> (19 pages).

Pfeifer et al. Improved EAF process control using on-line Offgas analysis. European Commission, 2011, ISBN; 978-92-78-22160-6. Retrieved from the Internet: <URL: http://bookshop.europa.eu/en/improved-eaf-process-control-using-on-line-offgas-analysis-pbKINA (170 pages).

European Patent Office; Extended European Search Report—EP 15832660.3; Tenova Goodfellow Inc.; Mar. 6, 2018; ; (7 Pages).

Canadian Patent Office; IPRP in respect of Application No. PCT/CA2015/000463; ; dated Dec. 15, 2016; Tenova Goodfellow Inc. (29 pages).

European Patent Office; EPO Communication Pursuant to Article 94(3) EPC dated Apr. 2, 2019; Tenova Goodfellow Inc.; (8 pages).

* cited by examiner

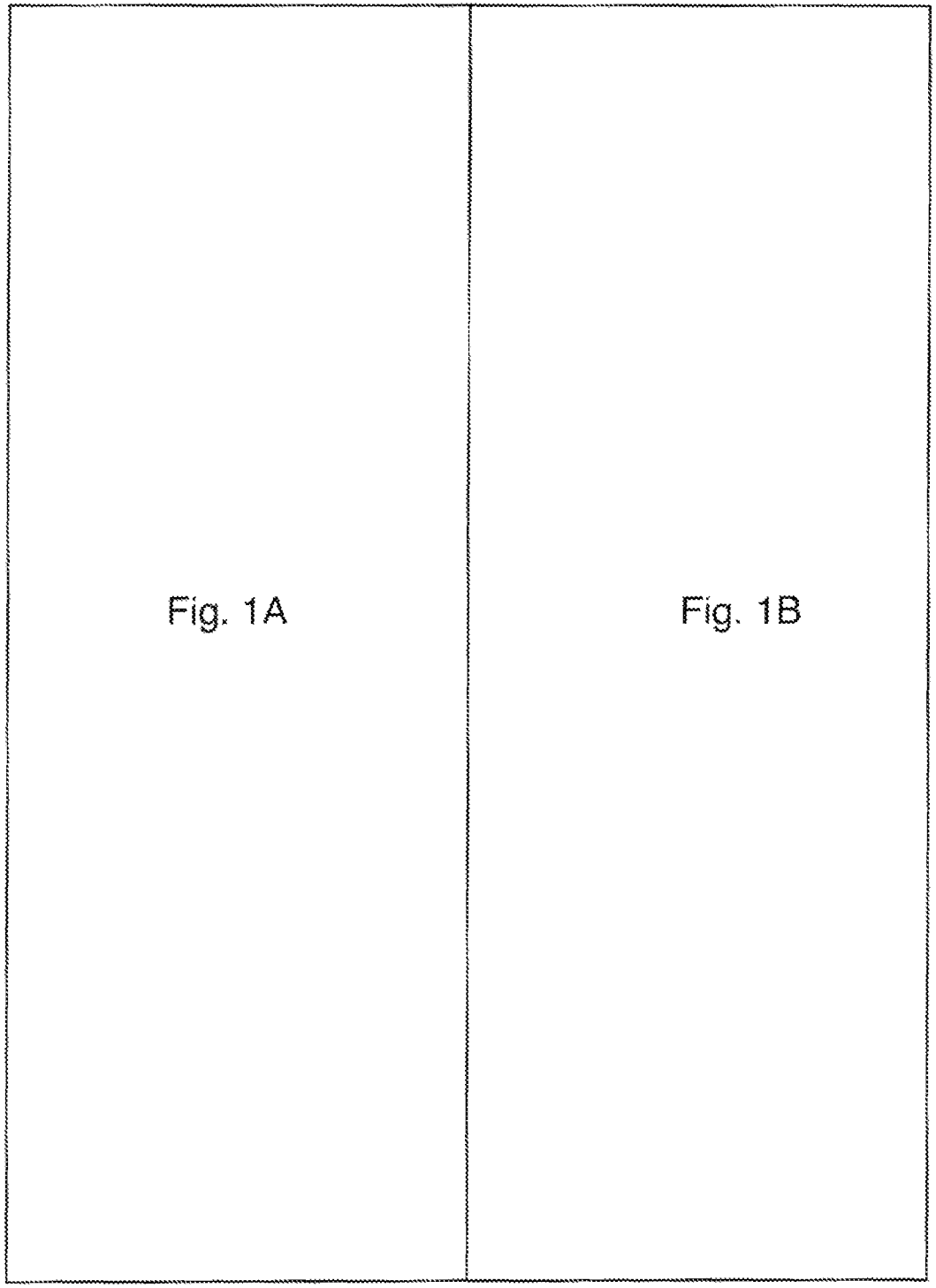

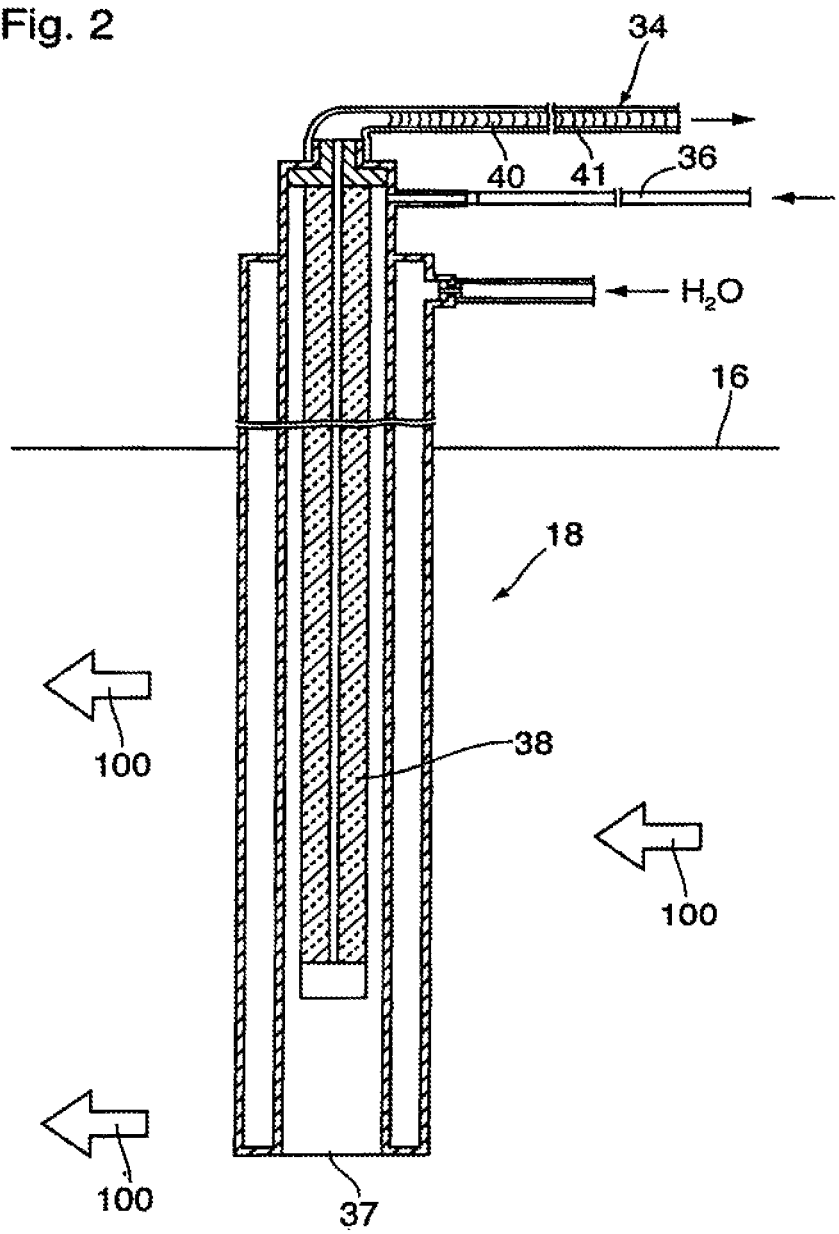

SYSTEM AND METHOD FOR ANALYZING DUSTY INDUSTRIAL OFF-GAS CHEMISTRY

RELATED APPLICATIONS

This application is a continuation of U.S. patent application Ser. No. 15/502,615 filed Aug. 14, 2015, which was submitted with a 371(c) date of Feb. 8, 2017 pursuant to 35 USC § 371 and as a United States national phase application of International Patent Application No. PCT/CA2015/000463, filed Aug. 14, 2015.

This application claims the benefit of 35 USC § 119(e) to U.S. Provisional Patent Application Ser. No. 62/037,821, filed 15 Aug. 2014, the disclosure of which is incorporated herein by reference.

SCOPE OF THE INVENTION

The present invention relates to a system and method of analyzing off-gases, and more particularly a system for the analysis of dusty or high-particulate industrial off-gas chemistry by performing the optical analysis of one or more off-gas components in proximity to an off-gas flue.

BACKGROUND OF THE INVENTION

Technology that continuously analyzes off-gas chemistry is an important tool for optimizing, controlling and improving the performance of combustion processes such as electric arc furnace (EAF) and basic oxygen furnace (BOF) steelmaking processes or the like.

In the EAF steelmaking process, full-spectrum off-gas analysis for CO, $CO_2$, $H_2$, $O_2$, $H_2O$ vapor and $N_2$ is a valuable tool for holistic optimization and control of the steelmaking process.

$N_2$ analysis is effective for assessing and dynamically controlling fume system suction to avoid both over and under drafting conditions CO, $H_2$, $O_2$ & $N_2$ analysis are effective for determining if the EAF is operating in an overly oxidizing or reducing atmosphere CO, $CO_2$ & $H_2$ analysis are effective for optimizing and dynamically controlling burners and for optimizing the charge carbon practice CO & $CO_2$ analysis are effective for optimizing and dynamically controlling carbon injectors CO, $H_2$ & $O_2$ analysis are effective for optimizing and dynamically controlling the oxygen lances $H_2$ & $H_2O$ vapor analysis are effective to determining the onset of a water panel leak into the furnace CO, $CO_2$, $H_2$, $O_2$, $H_2O$ vapor and $N_2$ analysis is required to close a real-time mass & energy balance for the EAF process Similarly, in the BOF steelmaking process having a full spectrum off-gas analysis for CO, $CO_2$, $H_2$, $O_2$, $H_2O$ vapor and $N_2$ is preferred to close a real-time mass & energy balance for the BOF process which is effective for controlling the efficiency of the oxygen blowing practice, controlling the amount and the timing of post combustion oxygen flow and determining when to terminate the oxygen blow because the aim steel carbon and temperature endpoints have been achieved.

To date, continuous off-gas analysis technology for industrial applications has remained essentially unchanged since about 1997 being based on one of two principle methods;
1. Extractive systems use a vacuum pump to continuously extract a sample of process off-gas through a probe positioned in the fume duct with said probe connected to a hollow often heated conduit that directs the off-gas sample to a continuous gas analyzer. E. J. Evenson U.S. Pat. No. 5,777,241 describes such an extractive system for optimization and control of steelmaking processes. Depending on the gaseous species to be analyzed, various analytical methods are employed with extractive technology including mass spectrometry which can analyze most gaseous species, non-dispersive infra-red (NDIR) which is a standard method for analyzing CO and $CO_2$, a solid state electrochemical cell and thermal conductivity which are standard methods for $O_2$ analysis and for $H_2$ analysis respectively.
2. In situ laser systems transmit a single beam or a combined beam or multiple individual beams within the visible, near and mid IR range through the off-gas as it flows in the fume duct for subsequent pick-up by an optical detector (s). D. K. Ottesen U.S. Pat. No. 5,984,998 and S. C. Jepson U.S. Pat. No. 6,748,004 present examples of in situ laser systems for measuring off-gas chemistry. In general, the transmitted lasers wavelength is modulated around the particular spectroscopic line of the gaseous species of interest. The amount of absorption in the detected beam is subsequently used to calculate the concentration of that particular species in the off-gas. Multiple lasers are required depending on the gaseous species to be analyzed, typically one near IR range laser with a suitable wavelength for $CO_2$ and $H_2O$ vapor, a second near IR range laser with a suitable wavelength for CO and a third visible range laser with a suitable wavelength for $O_2$. It is noted that three separate lasers of the correct wavelength are required to analyze CO, $CO_2$ and $O_2$. Because the CO and $CO_2$ absorption peaks begin to overlap as the off-gas temperature increases above about 300° C., in situ laser systems need to employ one near-IR range laser with a suitable wavelength for $CO_2$ and a separate second near-IR range laser for CO. A third visible range laser with a suitable wavelength is required for $O_2$. The in situ method can also utilize either the CO or $CO_2$ laser to analyze $H_2O$ vapor if required. Because varying amounts of particulate matter are present in most industrial process off-gas, there is the possibility that the laser beam will suffer from attenuation which will scatter or block the beam. In many industrial applications, said attenuation problems can be reduced but not completely eliminated by employing two horizontal or vertical probes that are continuously purged with an inert gas such as $N_2$ with one probe housing the laser beam emitters and the second probe housing the laser beam detectors. These two probes extend into the fume duct from opposite sides with one probes open end being in close proximity to the opposite probes open end which serves to reduce the path length that the beams must successfully traverse between emitter and detector and minimize laser beam attenuation problems associated with particulate matter interference.

Extractive and in situ laser technologies each have their respective advantages and disadvantages and hence neither technology provides a complete off-gas analysis solution;

Analytical capabilities: Extractive off-gas systems have the advantage of being able to utilize and combine a range of analytical methods to provide a virtually complete spectrum of off-gas chemistry. For example, steelmaking off-gas chemistry consists almost exclusively of six gaseous species which vary in concentration according to process dynamics; CO, $CO_2$, $O_2$, $H_2$, $H_2O$ vapor and $N_2$. For all practical purposes and unless a foreign gas is deliberately introduced into the furnace atmosphere, the concentration sum of these six gaseous species totals 100%. As explained earlier, various extractive analytical methods can be used to analyze for CO, $CO_2$, $O_2$, $H_2$ & $H_2O$ vapor. In the case of $N_2$, it can either be analyzed by extractive mass spectrometry or it can be calculated with reasonable precision by summing the analysis of the remaining five principle gaseous species and subtracting from 100%.

By comparison in situ laser systems can use a combination of lasers in the correct wavelength range to analyze specific gaseous species of interest. For example, for in situ analysis of high temperature off-gas such as for steelmaking applications, three separate lasers of different wavelengths will be required to analyze CO, $CO_2$, $O_2$ & $H_2O$ vapor. However, in situ laser technology is not technically capable of analyzing many mononuclear diatomic gases including $N_2$ and $H_2$ (S. Schilt, F. K. Tittel and K. P. Petrov, "Diode Laser Spectroscopic Monitoring of Trace Gases", Encyclopedia of Analytical Chemistry, pages 1-29, 2011). Hence, compared to extractive methods in situ laser technology has the disadvantage of limited analytical capabilities.

Analytical Precision: Extractive systems can tailor their analytical method to meet the analytical precision needed for specific industrial process control situations. Hence, extractive technology has the advantage of having the flexibility to tailor the analytical precision to the application requirements.

The analytical precision of laser systems is gas species dependent. The amount of absorption of the beam determines the analytical precision. Each gaseous species has an optimum beam path length that provides the optimum amount of absorption and the optimum analytical precision. In general, using a path length with the optimum absorption will meet the analytical precision needed for many industrial process control situations. However, path lengths that are shorter than the optimum will reduce the amount of absorption and the analytical precision. Conversely, too long a path length can result in signal saturation and limit the measurement span of the instrument. In situ lasers use a fixed path length defined as the distance between the laser beam emitter and detector. This fixed path length is common to all gaseous species being analyzed. As described previously, in situations where there are optical signal transmission difficulties due to beam attenuation in dusty industrial off-gas environments, in situ laser systems select the fixed path length to minimize laser interruptions by positioning two opposite facing inert gas purged probes. The separation distance between the open ends of said two probes defines the fixed path length that the laser beam must transmit through the process off-gas. Hence, compared to extractive methods which can be designed for high analytical precision for all gaseous species, the fixed, common path length used in in situ laser technology may or may not provide the required analytical precision for all gaseous species being analyzed.

Calibration: Most extractive analytical methods require periodic recalibration to compensate for analytical drift. Depending on the gases to be analyzed, extractive systems can require several specialized calibration gases which can be expensive. Hence, extraction technology has the disadvantage that the analytical methods require periodic recalibration and specialized calibration gases.

In situ laser systems are often equipped with reference cells that contain known concentrations of the gaseous species being analyzed. Laser technology uses the known reference cell gas composition to self-calibrate the system. Hence, compared to extractive methods, in situ laser technology has the advantage that it does not require periodic recalibration or specialized calibration gases.

Analytical Response Delay: The analytical response delay for extractive system depends on the residence time of the off-gas sample from the probe tip to the analytical cells located in the analyzer. The residence time is dependent on the volume of the gas train (probe, transport conduit & filtration system), the extraction flow rate of the gas and the physical distance between the probe and the analyzer which is often longer than desirable because of the need to house the analyzer in a large, environmentally protective enclosure. While extractive systems can use a high velocity pump to rapidly extract off-gas at high flow rate through the probe, often the analytical devices inside the analyzer are designed to use only a slower velocity gas flow rates and therefore the majority of the off-gas extracted sample is vented before the analyzer which uses only a slower velocity slip stream. All of these factors serve to increase the analytical response delay of extractive systems. Most modern extractive systems for example those used in the steel industry are designed to provide an analytical response within about 20 to 40 seconds from the time the gas enters the probe tip until the corresponding gas analysis is reported, In situ laser systems have a much shorter response delay of the order of 2 seconds because the off-gas is not physically transported to a remote analyzer. Hence, compared to extractive methods in situ laser technology has the advantage of a much shorter analytical response delay.

Analytical Reliability: Extractive off-gas systems can be categorized as "active" technology. Typically the extractive analysis system is interfaced with the furnace control network so that whenever the industrial process is producing off-gas, the extractive system automatically switches on a pump or the like to provide high suction to actively extract a sample of off-gas through the probe which is appropriately positioned in the fume duct. The off-gas sample is transferred at high flow rate through a hollow heated or unheated conduit to the analyzer. For dirty, humid off-gas as exists in many industrial processes, the hot, humid off-gas sample is first passed through a series of progressively finer filters to remove particulate matter from the off-gas sample. Since many analytical techniques mentioned previously require clean, dry gas for reliable chemical analysis, after filtration the process off-gas is typically passed through a condenser or the like to remove water vapor prior to analysis which is subsequently reported on a dry basis. In a few select situations such as when it is necessary to avoid formation of corrosive acids in the condensate or when analyzing some specific gaseous species such as water vapor, the cleaned off-gas sample maybe kept at a temperature above its dew point and analyzed wet. However, in such instances the analytical cells must be designed to operate reliably and precisely at elevated temperature. Extractive systems are typically designed to automatically and periodically switch to an active back-purge for example during periods when the industrial process is not producing off-gas. This automatic back-purge can consist of high pressure compressed air or inert gases such as $N_2$ or the like and are designed to clean the probe and filters of accumulated particulate matter. Historically, such extractive technology that alternates between positive suction and back-purging has demonstrated exceptional analytical reliability, for example when properly maintained, extractive technology applied for in harsh steelmaking process conditions has reportedly demonstrated better than 99% reliability to provide continuous off-gas chemistry from start-to-end of the steel producing heat.

By comparison, in situ laser systems can be categorized more as "passive" technology that relies on passive transmission of laser beam(s) through the off-gas fume from an emitter to a detector. Attenuation of the laser beam that prevents a sufficient level of detection will result in interrupted off-gas analysis. For example, under steelmaking process conditions, early in situ laser systems suffered from serious laser beam attenuation difficulties and lost signals because of significant amounts of dust prevalent in the harsh process off-gas. As discussed previously, various methods have been reported to reduce attenuation difficulties including the use of continuous inert gas purged, opposite facing horizontal or vertical probes to shorten the path length that the laser must successfully transmit through the dirty process gas, or, particulate deflectors or impingers such as disclosed by W. A. Von Drasek U.S. Pat. No. 6,943,886. While these devices have considerably reduced beam attenuation problems compared to original fill path length in situ designs, because of the passive nature of laser transmission there still remains a risk that one or more of the in situ laser beams may suffer from periodic and unpredictable interruptions in signal transmission especially when dust loading is particularly high. For example, steel industry reported information indicates that on average about 50% of EAF heats will experience some degree of lost laser signals due to fume signal interruption. Any lost laser signals during EAF scrap melting would limit effectiveness of off-gas water leak detection systems during critical melting periods when hung-up scrap can fall into bath and create a metal slosh event that can trigger a water leak related explosion. In addition laser signal interruption limits the effectiveness of process monitoring and control functions. Hence, compared to extractive methods in situ laser technology has the disadvantage of uncertain analytical reliability especially in harsh industrial situations such as steelmaking processes.

Installation and Maintenance Considerations: Most extractive analyzers used in harsh industrial situations must be housed within a protective room or enclosure that ensures the electronics are maintained within an acceptable working environment particularly regarding minimizing industrial dust and maintaining suitable ambient temperatures. If a suitable enclosure does not already exist within the plant, a protective room will need to be constructed which adds to the cost of installation. To minimize analytical response delays, the protective analyzer room needs to be located within close proximity (usually with ~30 meters) from the extraction probe. Depending on the particular circumstances, finding a suitably sized area in close proximity to the probe can be challenging in confined industrial spaces. Because extractive systems filter and usually dry the process off-gas prior to analysis, extractive systems require regular maintenance to inspect and replace clogged filters, to inspect and service pumps and condensers as well as discussed previously, to periodically check and adjust calibration to ensure analytical precision.

By comparison, in situ laser systems mount the laser beam emitters and receivers on the fume duct often inside protective path length shortening probes as discussed previously. The laser beam is usually transmitted to the emitter from a remotely located laser by fiber optic cable. The received signal after the beam has passed through the process off-gas is also transmitted electronically. As such, since the off-gas does not physically transfer to the lasers and signal analysis componentry, it can be located remotely without distance restrictions. In addition, in situ systems do not require filters, condensers or pumps. Hence, compared to extractive methods in situ laser technology has the advantage of lower installation costs and less maintenance requirements.

Process Control Functionality: The functionality of the off-gas analysis technology for optimizing, controlling and improving the performance of a combustion process will depend largely on the analytical capabilities of the off-gas analysis system. For example, the following table provides the key gaseous species analyses required to provide complete process control and optimization functionality in a steelmaking furnace. Hence applicant has recognized the extractive methods which provide a complete off-gas analysis spectrum have the advantage over the limited analytical capability provided by in situ laser technology.

SUMMARY OF THE INVENTION

In one aspect, the current invention involves a novel method never before reported in the prior art for analyzing dust containing, high temperature industrial off-gas. The current invention makes use of the advantages of the extractive and in situ laser methods, while avoiding many of their respective disadvantages as overviewed above. The novel aspects of the current invention as more fully described herein enable analytical response times of as short as about 8 seconds, as well as uninterrupted full spectrum analysis of $H_2O$ vapor, CO, $O_2$, $CO_2$ and $H_2$.

The invention provides in another aspect a system and method for analyzing off-gases, and preferably high temperature industrial off-gas, such as for example, dust laden industrial off-gases from steel making furnaces, smelters and the like. The invention may enable analytical response times of as short as 0.5 to 4 seconds in certain applications and/or more uninterrupted full spectrum analysis of a variety of off-gas components, including without limitation, $H_2O$ vapor, CO, $O_2$, $CO_2$ and/or $H_2$.

Most preferably, the system includes an off-gas analyzer which is electronically linked to plant or furnace control systems to regulate or vary plant or furnace operating parameters, in response to detected off-gas components.

In one embodiment, the system includes a suitably designed probe, and more preferably a fluid cooled gas sampling probe and associated gas extraction pump. The probe and pump are used to intermittently or continuously extract an off-gas sample from a selected sampling point along the furnace or fume duct, and to convey the gas-sample to a sampling station or analyzer for analysis.

Although not essential, most preferably the extracted off-gas sample is a wet off-gas sample, with the probe configured to extract gas samples from the furnace or fume duct whilst maintaining the extracted gas sample at a temperature selected to substantially prevent condensation of water vapour and/or gaseous phases therefrom. One preferred probe construction is described in commonly owned International Patent Application No. PCT/CA2014/000162, entitled "Non-Condensing Gas Sampling Probe System", the disclosure of which is incorporated herein in its entirety.

Where exhaust gas water vapour content is to be analysed, a hollow heated conduit is preferably also used to fluidically transfer the hot, wet off-gas sample from the probe to the analyzer/sampling station. In a simplified design, the heated conduit is provided with a resistance-type heater and covering insulation to maintain the extracted gas sample therein at an elevated temperature substantially preventing or minimizing water condensation therefrom. The sampling station may optionally include a heated gas sampling chamber which includes an optical measuring cell maintained at an elevated temperature above a dew point or condensation temperature of selected off-gas components, and most preferably a temperature of at least 100° C., and preferably about 130° C.±10° C. The sampling station and optic measuring cell are optically coupled to or provided with one or more coherent light sources or associated lasers. The lasers are operable to transmit coherent light beam energy to the measuring cell and through an extracted off-gas sample for analysis of one or more gas sample component concentrations. In another possible construction, the measuring cells are preferably optically coupled to a TDL laser operable to emit a coherent light beam in the IR, and preferably mid-IR range, by way of a fiber optic cable. The measuring cells are operable to analyze CO, $CO_2$, $O_2$, water vapour and/or $H_2$ concentrations in the extracted gas sample.

In another embodiment of the system, a suitably designed water cooled sample probe and associated pump may be used to continuously force extract a sample of off-gas from a fume duct. The water cooled probe has its open end positioned inside the fume duct. To minimize the delay time associated with extracting the off-gas sample through the probe, in the preferred embodiment of the current method, the probe incorporates a centrally located smaller diameter extraction line with the aperture of said extraction line being extended downwards to be in close proximity to the opening of the main body larger diameter probe. By using an extended smaller diameter extraction line, the residence time for extracting the off-gas sample through the probe is markedly reduced. This extraction line which is periodically back purged to remove particulate matter may also incorporate a suitably designed primary filter to further reduce fume infiltration. The extraction line may also be heated to maintain the off-gas temperature above the dew point temperature of the gas.

A hollow conduit also heated above the dew point temperature is subsequently used to continuously transfer the hot, wet off-gas sample from the probe to a nearby sampling station.

In the current system, the sampling station may be of novel design, and is preferably much more compact in size than the traditional analyzer unit associated with the conventional extractive method and has been designed to operate without the need for an environmentally protective room. Because of the compact nature of the sampling station and the absence of an associated environmentally controlled room, the sampling station can be positioned directly on the plant floor in very close proximity to the probe thereby further reducing response delays associated with transferring the off-gas.

The sampling station is configured to analyze gasses in two operational steps that greatly improve reliability and precision compared to the in situ optical method. First, the off-gas sample is cleaned of particulate matter with progressively finer filters. Second, the cleaned, wet gas is introduced into a series of specially designed analytical cells with each cell incorporating an optical transmitter connected by fiber optic cable to a remote tunable diode laser which generates a beam of the correct wavelength for the gas species being analyzed by said cell, and, an optical detector connected by coaxial cable to a remote signal analysis unit. Unlike the fixed path length used to analyze all gaseous species in the in situ laser method, in the current method, the length of each analytical cell in the sampling station is tailored to the optimum laser transmission length needed to meet the required analytical precision for the specific gas being analyzed in accordance with the analytical requirements of the industrial application. Furthermore, the laser used in the current method does not require regular calibration checks or calibration gases as with the current extractive method.

Filtering the off-gas to remove particulate prior to introducing the off-gas sample into the analytical cells represents a major advancement over the current in situ method. The use of clean gas greatly reduces problems associated with laser beam attenuation and interrupted signals. Furthermore, eliminating the laser attenuation problems allows the length (L) of each analytical cell to be tailored to the optimum laser transmission length needed to satisfy the analytical precision requirements for each gaseous species because there is no concern with laser beam attenuation and scattering from particulate matter in the off-gas sample.

Although not essential, most preferably the sampling station is provided with a suitable heat source, such as quartz or resistance coil heater. The heat source is used to heat at least analyzing portions of the chamber interior to assist in maintaining the extracted gas sample therein at a constant temperature, preferably the same as when initially extracted, as it moves through optical measuring cells.

The sampling station may be provided housed within a stand-alone cabinet, and which has a more compact in size compared to conventional gas analyzer units associated with conventional extractive methods. In one simplified design, a thermally divided cabinet having heated and unheated or cooled sections is provided. In a most preferred construction, the cabinet has both height and width dimensions less than about 150 cm, and preferably between about 50 to about 100 cm, and a cabinet depth ranging from about 10 cm to about 50 cm.

Because of the compact nature of the sampling station cabinet and the absence of an associated environmentally controlled room, the sampling station can be positioned directly on the plant floor in close proximity, and preferably within 1 to 50 metres, preferably within 2 to 15, and more preferably within 5 to 10 metres to the probe. The positioning of the sampling station in such close proximity advantageously reduces sample delivery distance, minimizing sample degradation and response delays associated with the transfer of off-gas samples prior to analysis. Further, by locating the sampling station in such proximity to the probe and gas extraction point, cooling and/or precipitation of vapour and/or loss of volatile phases from wet extracted gas samples prior to analysis may be minimized.

The sampling station may further be provided with one or more particulate filters, wherein gas samples fed into the sampling station are initially further cleaned of particulate matter. Most preferably, a series of progressively finer filters provided upstream from the optic measuring cells through which the extracted off-gas sample passes as it is fed into and through prior to passing through or into one or more optical measuring cells for analysis.

In a preferred embodiment, the analytical cells are also designed to operate at a temperature above the off-gas dew point thereby avoiding the need for an additional off-gas condensation step. This eliminates the need for a condenser which further reduces the physical size of the sampling station. In addition, by analyzing wet off-gas, optimizing the design of each specific analytical cell and using proprietary software in the signal analysis unit, the current invention also enables full spectrum analysis of $H_2O$ vapor, CO, $O_2$, $CO_2$ and $H_2$. In many metallurgical and combustion applications, having such a full spectrum analysis enables the concentration $N_2$ to be determined by difference from 100%.

The current invention also enables a simplified and effective arrangement for analyzing off-gas compositions at multiple sample points by connecting each sampling point's compact sampling station by fiber and coaxial cables to a common laser generator and signal analyzing unit equipped with a suitable multiplexer or splitter that distributes the optical signals between the respective sampling stations.

In the current method, a multipoint optical analyzer is connected by fiber optic cables to the specially designed laser cells contained in the sampling station which is located in close proximity to the probe. The optical analyzer is designed to contain multiple tunable diode lasers that generate laser beams in the desired wavelength range specific to each gaseous species being analyzed which may include but is not limited to gases such as CO, $CO_2$, $O_2$ and $H_2O$ vapor. The corresponding signals from these laser cells are electronically returned to the remote optical analyzer for signal analysis to determine the gases composition. The sample station can also be designed to house other analytical devices such as specially designed thermal conductivity cells and electrochemical cells as maybe required to provide additional analytical capabilities in tune with the needs of the industrial application. These additional sensors have been specially designed to analyze wet off-gas by operating above the dew point temperature of the gas thereby eliminating the need for a condenser as required in the extractive technology. In addition, these sensors have been specially designed to operate without the need for calibration gases.

As noted earlier, the optical analyzer is designed to have multipoint analytical capabilities and can analyze signals from up to but not limited to 8 separate sampling stations which makes the current method ideally suited for industrial applications with multiple furnaces or off-gas sampling points.

Although not essential, multiple sampling chambers are preferably fluidically connected in series or in a parallel arrangement, and may be provided as part of a modular unit which is removable and interchangeable, allowing the sampling station to be easily tailored specifically to the specific desired off-gas components to be analyzed. Each cell sampling chamber is formed with a length (L) corresponding to a desired absorption profile of the target off-gas component to be analyzed and includes an associated optical transmitter or emitter and an associated optical detector. With each sampling chamber, the length (L) between the optical transmitter and the associated detector is tailored to the optimum emitted coherent light beam transmission length selected to meet the desired analytical precision for a chosen specific or target gas component to be analyzed, in accordance with the analytical requirements of the individual industrial application. The lasers used with the system do not require regular calibration checks or calibration gases emitters of each measuring cell as with the existing extractive method. Rather the optical emitters in each cell are connected by fiber optic cables to one or more remotely located tunable diode lasers. The lasers are operable to generate and emit from each optical transmitter a coherent light beam, and preferably a beam in the mid-IR, near-IR and visible range of the correct wavelength for the specific gas species being analyzed by the sampling chamber. The associated optical detectors in each sampling chamber are positioned to receive and convert the collected emitted beam energy into data which is transmitted electronically by coaxial cable to a remote signal analysis unit and/or furnace control.

In addition the optical cell sampling chamber is designed to minimize the internal volume so to reduce the gas resident time in the cell and the associate delay.

In another embodiment, the measuring cell may be provided with one or more sampling chambers adapted to receive a multiplexed laser beam. The multiplexed beam comprising a collimated beam from multiple laser sources which is optically transmitted by way of a single fiber optic cable, and which upon detection by the cell is subsequently de-multiplexed for gas component analysis.

Accordingly, in a first aspect the present invention resides in an off-gas analyzer apparatus for measuring gas components of a gas sample to be analyzed, the apparatus comprising, a gas component measuring cell comprising, first and second elongated sampling chambers, said sampling chambers being in fluid communication a gas inlet for receiving said gas sample to be analyzed, said first and second sampling chambers extending from a respective first end to a second end spaced therefrom, said sampling chambers having a respective length correlated to an absorption profile of an associated target gas component of said gas sample to be analyzed, an optical head being positioned towards the sampling chamber first ends, the optical head adapted for optical coupling to a coherent light source and including a plurality of emitters, said emitters being positioned to emit a coherent light beam along an associated sampling chamber, a detector assembly being positioned towards the sampling chamber second ends, the detector assembly provided for electronic coupling to a gas analyzer and including at least one detector for receiving said coherent light beams emitted from said emitters, a filter assembly for filtering particulate matter from said gas sample prior to analysis by said gas component measuring cell, and a gas conduit assembly substantially providing fluid communication between a gas sample source and said filter assembly, and from said filter assembly and said gas inlet.

In a second aspect, the present invention resides in an off-gas analysis system for measuring gas components of a gas sample from a furnace off-gas stream, the system comprising, a gas analyzer apparatus, a processor, a coherent light source, and a gas conduit assembly for fluidically communicating said gas sample from a sampling point in said off-gas stream to said gas analyzer apparatus, the gas analyzer apparatus including, a gas component measuring cell comprising, a gas inlet fluidically communicating with said gas conduit assembly, a plurality of elongated sampling chambers, said sampling chambers being in fluid communication the gas inlet for receiving said gas sample therethrough, said sampling chambers extending from a respective first end to a second end spaced therefrom, said sampling chamber having a respective length correlated to an absorption profile of an associated target gas component of said gas sample to be analyzed, an optical head being position towards the sampling chamber first ends, the optical head provided for optical coupling to said coherent light source and including a plurality of emitters, said emitters being positioned to emit a coherent light beam substantially along as associated sampling chamber, a detector assembly electronically communicating with said processor and including a plurality of optical detectors, said detectors being positioned towards an associated sampling chamber second end for detecting and converting non-absorbed portions of said associated coherent light beam as electric signals, a filter assembly in fluid communication with said conduit assembly and said gas component measuring cell, the filter assembly disposed in an upstream position from said gas inlet for filtering particulate matter from said gas sample prior to analysis in said gas component measuring cell.

In a third aspect, the present invention resides in a furnace gas analysis and control system comprising, at least one gas analyzer apparatus operable to measure selected gas components of an extracted furnace off-gas sample, a system processor electronically communicating with each said gas analyzer and operable to output furnace control signals in response to the measured gas components detected thereby, a coherent light source, and a gas conduit assembly in fluid communication between a selected sampling point in said off-gas stream and an associated said gas analyzer apparatus, each said gas analyzer apparatus including, a gas component measuring cell comprising, a gas inlet and gas outlet, a plurality of elongated sampling chambers for receiving the extracted off-gas sample therein, said sampling chambers fluidically communicating with each other and said gas inlet, the sampling chambers extending respectively from a first end to a second end spaced therefrom, and having a respective length correlated to an absorption profile the selected gas component of said off-gas sample to be analyzed, an optical head being positioned towards the sampling chamber first ends, the optical head provided for optical coupling to said coherent light source and including a plurality of emitters, said emitters being positioned to emit a coherent light beam along an associated sampling chamber, a detector assembly comprising an optical detector positioned towards each associated sampling chamber second end for detecting and converting non-absorbed portions of said associated coherent light beam into electric signals, and a filter assembly disposed in an upstream position from said gas inlet for filtering particulate matter from said extracted off-gas sample prior to analysis in said gas component measuring, a pump assembly operable to convey said off-gas samples from said selected sampling points to the gas inlet of selected said gas analyzer apparatus.

In addition to the foregoing, the present invention also provides for numerous additional non-limiting aspects and which include:

An off-gas analyzer apparatus according to any of the preceding aspects, wherein said gas component measuring cell comprises first and second removable windows spaced towards and substantially sealing respectively each of the first and second ends of the sampling chambers.

An off-gas analyzer apparatus according to any of the preceding aspects, wherein said emitters further comprise a collimator selected to emit said coherent light beam as a collimated light beam along said associated sampling chamber, and said detector assembly further comprises a lens associated with each said sampling chamber for refocusing each said collimated light beam towards an associated said detector.

An off-gas analyzer apparatus according to any of the preceding aspects, wherein said first and second sampling chambers comprise generally axially aligned longitudinally extending cylindrical chambers, said chambers being provided in fluidic communication along substantially their entire longitudinal length, said gas inlet being fluidically coupled to said first sampling chamber adjacent to said first chamber first end, and a gas outlet being fluidically coupled to said second sampling chamber adjacent to said second chamber second end.

An off-gas analyzer apparatus according to any of the preceding aspects, wherein said gas component measuring cell is provided as a modular removable unit.

An off-gas analyzer apparatus according to any of the preceding aspects, further comprising a pump assembly operable to convey said gas sample from said gas sample source through said filter assembly and into said measuring cell for analysis.

An off-gas analyzer apparatus according to any of the preceding aspects, wherein said off-gas analyzer comprises a cabinet, said gas component measuring cell, said pump assembly and said filter assembly being substantially housed within said cabinet.

An off-gas analyzer apparatus according to any of the preceding aspects, wherein said cabinet comprises a heated compartment, and a heater assembly thermally communicating with said heated compartment, said gas component measuring cell being housed substantially within an interior of said heated compartment, and wherein said heater assembly is operable to maintain said heated compartment interior at a temperature of between about 105° C. and 130° C.

An off-gas analyzer apparatus according to any of the preceding aspects, wherein said coherent light source comprises a plurality of tunable diode lasers, said lasers being provided for optical coupling to an associated emitter.

An off-gas analyzer apparatus according to any of the preceding aspects, wherein said gas sample comprises an off-gas sample from a steel making furnace off gas stream, and said target gas component is selected from the group consisting of $N_2$, $CO$, $CO_2$, $H_2$, water vapour, and $O_2$.

An off-gas analyzer apparatus according to any of the preceding aspects, wherein the cabinet further includes an unheated compartment, the pump assembly including a pump motor being housed substantially within an interior of the unheated compartment.

An off-gas analysis system according to any of the preceding aspects, wherein said gas conduit assembly includes an elongated sampling probe for extracting said off-gas sample from a generally central portion of said furnace off-gas stream, and a heated conduit fluidically coupling said probe and said gas analyzer, the heated conduit operable to convey said extracted gas sample from said probe to said gas analyzer apparatus as a heated gas sample at a temperature selected at between about 80° C. and 150° C.

An off-gas analysis system according to any of the preceding aspects, wherein said gas component measuring cell comprises first and second removable windows spaced towards each of the first and second ends of the sampling chambers.

An off-gas analysis system according to any of the preceding aspects, wherein said emitters further comprise a collimator operable to emit said coherent light beam as a collimated light beam, and said detector assembly further comprises a lens associated with each said sampling chamber, said lens configured to refocus the emitted collimated light beam towards the associated optical detector.

An off-gas analysis system according to any of the preceding aspects, wherein the plurality sampling chambers include first and second generally cylindrical chambers, said first and second cylindrical chambers being provided in fluid communication along longitudinally extending edge portions, said gas inlet being fluidically coupled to said first cylindrical chamber adjacent to said first chamber first end, and a gas outlet being fluidically coupled to said second cylindrical chamber adjacent to said second chamber second end.

An off-gas analysis apparatus or system according to any of the preceding aspects, wherein said gas conduit assembly comprises a heated gas conduit having a length selected at up to 50 metres, and preferably between about 2 and 15 metres.

An off-gas analysis system according to any of the preceding aspects, further comprising a pump assembly operable to convey said gas sample from said gas sample source through said filter assembly and into said sampling chamber for analysis.

An off-gas analysis system according to any of the preceding aspects, wherein said gas analyzer apparatus further includes a cabinet comprising a heated compartment, and a heater assembly thermally communicating with said heated compartment, said gas component measuring cell being housed substantially within an interior of said heated compartment, and wherein said heater assembly is operable to maintain said heated compartment interior at a temperature of between about 105° C. and 140° C.

An off-gas analysis system according to any of the preceding aspects, wherein the cabinet further includes an unheated compartment, the pump assembly including a pump motor being housed substantially within an interior of the unheated compartment.

An off-gas analysis system according to any of the preceding aspects, wherein said coherent light source comprises a plurality of tunable diode lasers, each said laser being provided for optical coupling to an associated emitter.

An off-gas analysis system according to any of the preceding aspects, wherein said off-gas system comprises a steel making furnace off gas stream, and said gas components are selected from the group consisting of $N_2$, CO, $CO_2$, $H_2$, water vapour, and $O_2$.

A furnace gas analysis and control system according to any of the preceding aspects, wherein the at least one gas analyzer apparatus includes a first analyzer apparatus and a second analyzer apparatus, the coherent light source comprises a plurality of tunable diode lasers, and a switching assembly is operable to selectively optically couple said lasers and associated one of said emitters of a selected one of said first and second analyzer apparatus.

A furnace gas analysis and control system according to any of the preceding aspects, wherein said gas component measuring cell comprises first and second removable windows spaced towards and substantially sealing respectively each of the first and second ends of the sampling chambers, and each of the sampling chambers comprising a generally co-axially aligned cylindrical chamber, the sampling chambers being in fluid communication along longitudinally extending adjacent edge portions.

A furnace gas analysis and control system according to any of the preceding aspects, wherein said emitters further comprise a collimator selected to emit said coherent light beam as a collimated light beam along said associated sampling chamber, and said detector assembly further comprises a lens associated with each said sampling chamber for refocusing each said collimated light beam towards an associated said detector.

A furnace gas analysis and control system according to any of the preceding aspects, wherein said gas conduit assembly comprises an associated heated gas conduit providing fluid communication between each selected sampling point and each associated said gas analyzer apparatus, each associated heated gas conduit having a length selected at between about 2 and 15 metres.

A furnace gas analyzer and/or analysis and control system according to any of the preceding aspects, wherein said gas component measuring cell is provided as a replaceable modular unit.

A furnace gas analysis and control system according to any of the preceding aspects, wherein each gas analyzer apparatus is housed substantially within an associated cabinet, each said cabinet comprises a heated compartment, and a heater assembly thermally communicating with said heated compartment, said gas component measuring cell being housed substantially within an interior of said heated compartment, said cabinet having width, length and height dimensions each selected at between about 0.1 and 2 metres.

A furnace gas analysis and control system according to any of the preceding aspects, comprising a plurality of said gas analyzer apparatus, and wherein said furnace comprises a steel making furnace, and said selected gas component is selected from the group consisting of $N_2$, CO, $CO_2$, $H_2$, water vapour, and $O_2$.

A furnace gas analysis and control system according to any of the preceding aspects, wherein each said gas analyzer apparatus further includes a water vapour sensor fluidically communication with said gas component measuring cell for sensing water vapour concentration in said sample.

A furnace gas analysis and control system according to any of the preceding aspects, wherein said water vapour sensor is disposed in said heated compartment of said cabinet.

Use of a furnace gas analysis and control system according to any preceding aspect, or comprising a plurality of the off-gas analyzer apparatus according to any preceding aspects, at least one coherent light source for optically communicating coherent light to the off-gas analyzer apparatus, and a system processor electronically communicating with each said off-gas analyzer apparatus and the at least one coherent light source, wherein, the gas conduit assembly of a first said off-gas analyzer being provided in fluid communication with a first sampling location along a furnace off-gas fume duct for receiving associated extracted gas samples therefrom, and the gas conduit assembly of a second said off-gas analyzer being provided in fluid communication with a second sampling location along the furnace off-gas fume duct for receiving associated extracted gas samples therefrom, and wherein said second sampling station is spaced from said first sampling station, and wherein in use, following the extraction and communication of the associated extracted gas sample, into the sampling chambers of the first gas analyzer, with said system processor, actuating said first off-gas analyzer to emit coherent light beams from at least one said coherent light source along the sampling chambers, and by the detector assembly, detecting and measuring the emitted coherent light beams in the sampling chambers as an absorption profile of an associated target off-gas component selected from the group consisting of $N_2$, CO, $CO_2$, $H_2$, $O_2$ and water vapour at said first sampling locations, and following the extraction and communication of the associated extracted gas samples to the sampling chambers of the second gas analyzer, with the system processor, actuating said second off-gas analyzer to emit coherent light beams from at least one said coherent light source along the sampling chambers, and by the detector assembly, detecting and measuring the emitted coherent light beams as an absorption profile of the associated target off-gas component at said second sampling location, and comparing the measured absorption profiles of the target off-gas components and the first and second sampling locations, and generating furnace control signals based on the comparison.

Use of the furnace gas analysis and control system according to any of the preceding aspects wherein the system processor is operable to preferentially actuate one or more of said off-gas analyzers by increased time and/or frequency to effect a gas sample analysis which is weighted to one or more sampling locations along the furnace off-gas fume duct.

Use of the furnace gas analysis and control system according to any of the preceding aspects further wherein during actuation of the first off-gas analyzer, maintaining a temperature in the sampling chambers above a dew point of the associated extracted gas sample, and wherein at least one associated target off-gas component comprises water vapour.

Use of the furnace analysis and control system according to any of the preceding aspects wherein the furnace gas analysis and control system further includes an optical switching assembly operable to selectively optically couple at least one said coherent light source and the optical head of the first off-gas analyzer and/or the second off-gas analyzer, the system processor being operable to selectively actuate a selected one of the first and second off-gas analyzer apparatus, and operating the optical switching assembly to optically couple the at least one coherent light source to each of the first and second off-gas analyzer when selectively actuated.

Use of the furnace gas analysis and control system according to any of the preceding aspects wherein said coherent light source comprises a tunable diode laser.

Advantages of the Current Invention

The applicant has appreciated that various preferred features of the current invention may combine to achieve one or more non-limiting advantages and which may include:

Analytical Capabilities: Unlike in situ laser systems that provide only a partial off-gas analysis, the current invention may incorporate laser cells together with other analytical devices as required into a sampling station which are operable to analyze full or more complete spectrum off-gas chemistry. For example, in steelmaking furnace applications, the current invention is preferably designed to analyze 5 gaseous species CO, $CO_2$, $O_2$, $H_2$ and $H_2O$ vapor, and thereby may be operable to determine $N_2$ concentration by difference analysis, as explained previously.

Analytical Precision: Unlike in situ laser systems that use a fixed path length to analyze all gaseous species with said fixed path length determined as a compromise between analytical precision and minimized laser beam attenuation problems, in a preferred aspect the current invention may incorporate individual laser measuring cells which may be tailored for the sampling for each gaseous species being analyzed. Preferably, individual laser cells are tailor designed to provide the optimum laser transmission length needed to satisfy the analytical precision requirements for each gaseous species.

Calibration: Unlike extractive systems which require routine calibration checks and expensive specialized calibration gases, the use of laser measuring cells and other analytical devices may avoid the requirement of manual calibration checks or specialized calibration gases.

Analytical Response Delay: Unlike extractive systems which have lengthy response times often of the order of 20 to 40 seconds, the current system advantageously may utilize a high velocity pump to extract the off-gas sample at relatively higher flow rates, and/or through probes, which in the preferred embodiment incorporate a centrally located, smaller diameter extraction line. Apertures into the extraction line may be extended downwards to be in close proximity to the opening of the main body larger diameter probe. Off-gases may be directed at high velocity to a small sized sampling station that can be positioned directly on the shop floor and without the need for protective room, removing space considerations that hinder the positioning of conventional sampling stations in close proximity to the probe. Unlike extractive analyzers which use only a small fraction of the gas flow extracted from a slip stream, the laser measuring cells and other analytical devices located inside the sampling station are preferably designed to facilitate the high flow off-gas at rates of nominally but not necessarily up to 40 liters per minute, reducing the analytical response delay of the current invention to about 8 seconds or less.

Analytical Reliability: Unlike the in situ laser systems that rely on passive transmission of laser beam(s) through the off-gas fume from an emitter to a detector and can suffer from attenuation of the laser beam that prevents a sufficient level of detection resulting in interrupted off-gas analysis, the current invention has very high analytical reliability which may be equivalent or better than the extractive systems. The current invention is "active" technology that uses forced extraction that ensures a sample of off-gas is delivered to the analytical measuring cells. Unlike in situ laser methods, reliability of laser beam transmission is enhanced by first filtering the off-gas sample through a series of filters selected to remove particulate matter before introducing the filtered gases into the laser measuring cells.

The current method is interfaced with the furnace control network so that whenever the industrial process is producing off-gas, the current invention automatically switches on a pump to provide high suction to actively extract a sample of off-gas through the probe, and deliver it at high velocity to the sampling station for filtration and analysis. When the industrial process is in standby mode and not producing off-gas, the current system may operate to automatically switch to a filter and probe back purge to remove any accumulated particulate matter.

Installation and Maintenance Considerations; Extractive systems have higher installation costs and require more maintenance than in situ systems. The current invention allows for the use of a more compact sampling station that can be located directly on the shop floor, avoiding the installation costs and complexities of installing a large analyzer in an environmentally protective enclosure. The current method also allows for analysis of filtered wet, hot gases, and thereby may avoid the maintenance required to service a water vapor condenser. In addition the current invention minimizes the need for manual calibration checks or specialized calibration gases.

Process Control Functionality: Unlike the in situ laser method which cannot provide a full spectrum off-gas chemistry, in a preferred aspect, the invention is designed to provide full spectrum off-gas analysis, including but not limited to CO, $CO_2$, $O_2$, $H_2$ and $H_2O$ vapor.

For example, the following table provides the analytical capabilities of the various off-gas analysis technologies together with the key gaseous species analyses required to provide complete process control and optimization functionality in a steelmaking furnace. As shown, most preferably the current system provides a full spectrum off-gas analysis, including the analysis of $N_2$ by difference, without many of the disadvantages of conventional extractive technology. The current invention may thus provide a more complete off-gas analysis spectrum having the advantage over the limited analytical capability provided by in situ laser technology, and which is not technically capable of analyzing many mononuclear diatomic gases including $N_2$ and $H_2$ (S. Schilt, F. K. Tittel and K. P. Petrov, "Diode Laser Spectroscopic Monitoring of Trace Gases", Encyclopedia of Analytical Chemistry, pages 1-29, 2011).

| Off-Gas Analysis Method Analytical Capabilities | Off-Gas Species | | | | | |
|---|---|---|---|---|---|---|
| | CO | $CO_2$ | $O_2$ | $H_2$ | $H_2O$ | $N_2$ |
| Current System | ✓ | ✓ | ✓ | ✓ | ✓ | ✓ |
| Extractive Systems | ✓ | ✓ | ✓ | ✓ | ✓ | ✓ |
| In situ Laser System—equipped with 1 laser | ✓ | | | | ✓ | |
| In situ Laser System—with 2 lasers | ✓ | ✓ | | | ✓ | |
| In situ Laser System—with 3 lasers | ✓ | ✓ | ✓ | | ✓ | |
| Steelmaking Process Function | | | | | | |
| Process is oxidizing or reducing | ✓ | ✓ | ✓ | ✓ | | |
| Gas burner firing control & optimization | ✓ | ✓ | | ✓ | | |
| Carbon combustion control & optimization | ✓ | ✓ | | | | |
| Oxygen lancing control & optimization | ✓ | ✓ | ✓ | ✓ | | |
| Fume system suction to control air ingress | | | | | | ✓ |
| Water leak detection | | | | ✓ | ✓ | |
| Close a real-time Mass & Energy Balance | ✓ | ✓ | ✓ | ✓ | ✓ | ✓ |

BRIEF DESCRIPTION OF THE DRAWINGS

Reference is now made to the following detailed description taken together with accompanying drawings in which:

FIG. 2 illustrates schematically a gas extraction probe used in the analysis and control system of shown in the partial views of FIGS. 1A and 1B;

DETAILED DESCRIPTION OF THE PREFERRED EMBODIMENTS

Figure 1A:
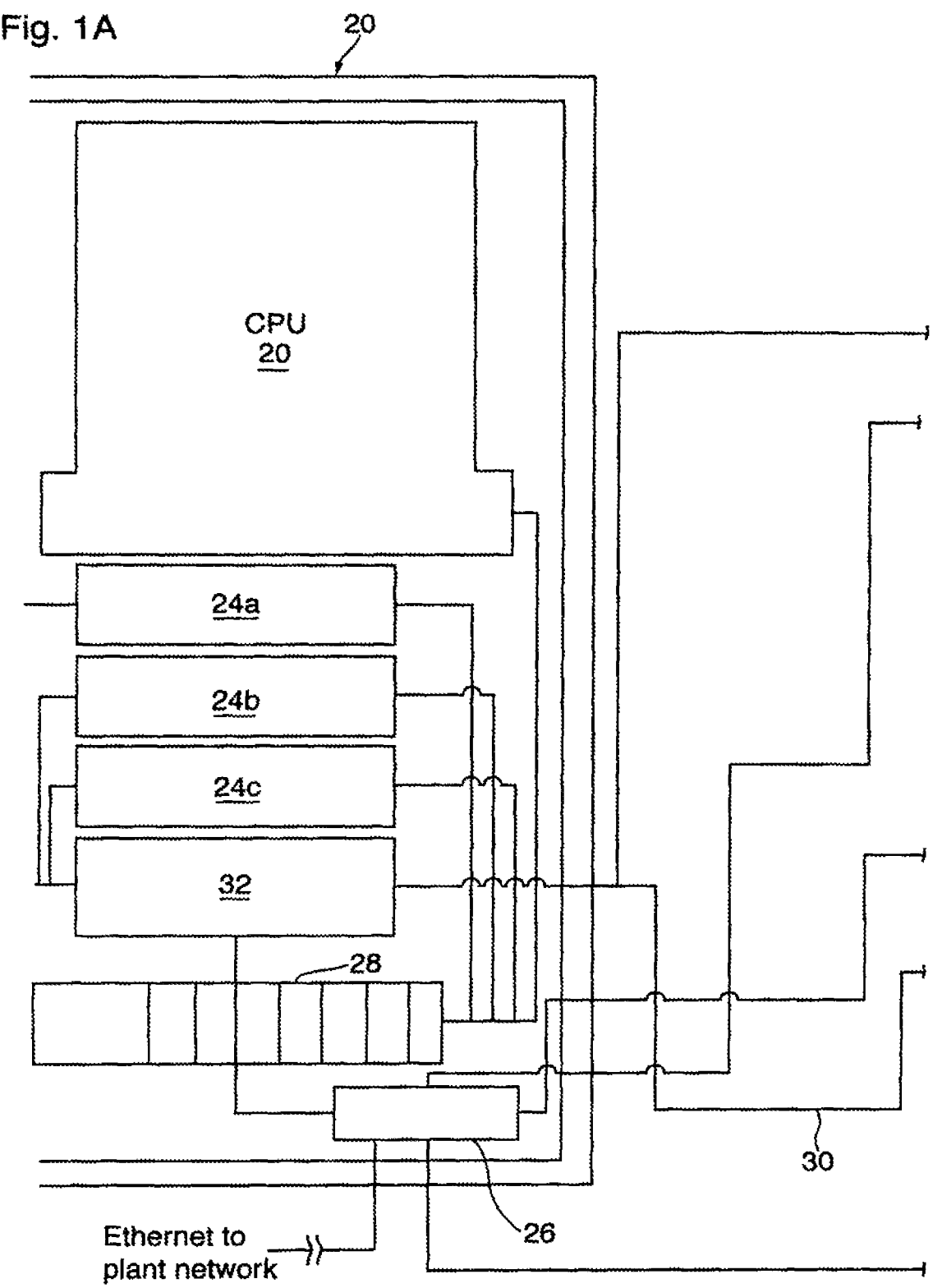
FIGS. 1A and 1B illustrate schematically particular views showing a furnace gas analysis and control system in accordance with a preferred embodiment of the invention.
Figure 1B:
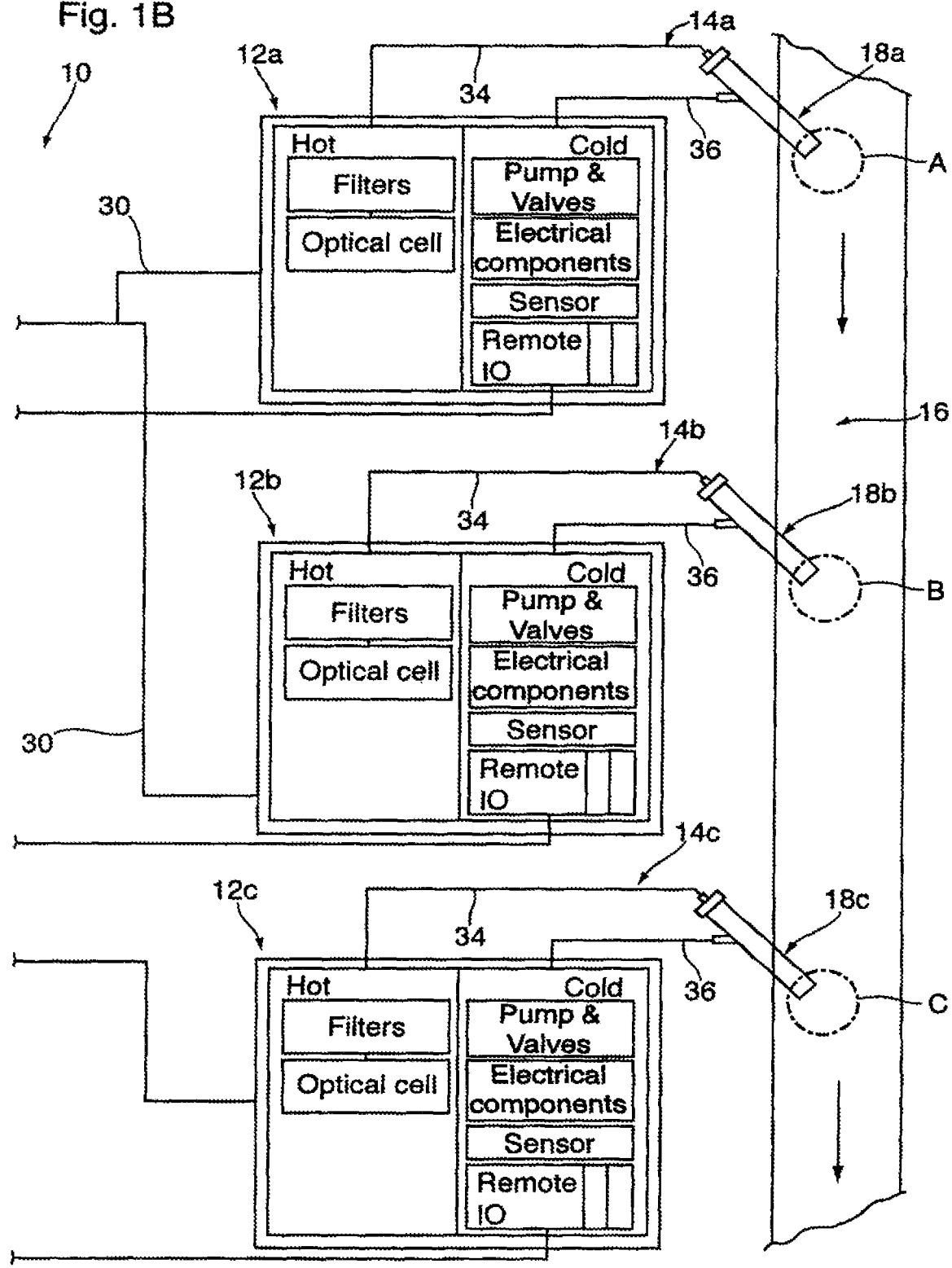

Reference may be had to FIGS. 1A and 1B which illustrate partial views of a furnace gas analysis and control system 10 used in the off-gas analysis and control of an industrial steel making furnace, in accordance with a preferred embodiment of the invention. As shown best in FIGS. 1A and 1B, the system 10 includes three gas sampling analyzers 12a,12b,12c which are optically and electronically connected to a control unit 20, by way of a suitable bi-strand fiber optic/coaxial cable 30. Each of the sampling analyzers 12a,12b, 12c are further provided in gaseous communication with a furnace gas fume duct 16 by an associated gas extraction conduit assembly 14a, 14b, 14c.

As illustrated, each conduit assembly 14a,14b,14c is provided with a gas extraction probe 18a18b,18c positioned at a respective pre-selected off-gas extraction sampling point A,B,C provided at longitudinally spaced locations along the furnace fume duct 16.

The system control unit 20 may be provided in a location remote from the sampling analyzers 12a,12b,12c, and preferably at a location isolated from both high furnace temperatures and dust. The control unit 20 includes a processor 22 such as a CPU, three tunable diode lasers (TDLs) 24a,24b,24c which are operable to output a coherent light beam in the mid-IR range, an optical switching unit 26, a programmable logic controller (PLC) 28, and a multiplexer/de-multiplexer 32.

As will be described, the optical switching unit 26, in conjunction with the multiplexer/de-multiplexer 32 and fibre optic/coaxial cables 30 is used to selectively optically and electronically couple the lasers 24a,24b,24c to each gas sampling analyzer 12a,12b,12c, depending on the desired sampling point A,B,C, from which an off-gas sample is to be extracted and analyzed. Most preferably, the fiber optic/coaxial cables 30 are provided with a secondary coaxial conduit used to transmit electron signals from the gas sample analyzers 12a,12b,12c to logic controller and CPU 22 for control of both the switching unit 26, and depending on the data received, furnace plant operational control. While the use of a multiplexer/de-multiplexer 32 advantageously permits lasers 24a,24b,24c to be optically connected to separate analyzers 12a,12b,12c, in an alternative construction, one or more optical splitters could be used to allow output laser beam energy to be split and separately simultaneously transmitted to multiple analyzers 12a,12b and/or 12c at lower power levels.

In one possible mode of operation, the gas extraction probes 18a, 18b,18c are positioned along the fume duct 16 at preselected extraction points A,B,C which are prioritized in relation to the importance of the selected gas component analysis to be performed by each associated sampling analyzer 12a,12b,12c, in assessing overall furnace operational performance. In operation, the control unit processor 22 is used to selectively activate and control each gas sampling analyzer 12a,12b,12c to extract an off-gas sample by way of the associated probe 18a,18b,18c, and analyze one or more target gas components therein at the selected extraction points A,B,C. It is envisioned that in a preferred mode of operation, the processor 22 may be used to effect the weighted gas sample extraction and analysis either more frequently and/or for longer periods of time at the critically most important gas sampling point A, than as compared with the extraction and analysis performed at: secondary sampling points B and C. In this manner, in one possible mode of operation, the processor 22 may be used to activate the sampling analyzers 12a,12b,12c so as to effect weighted sample extraction and analysis from the individual sampling points in the order A,B,A,C,A,A,C. It is to be appreciated that in an alternate mode of operation, each of the sampling analyzers 12a,12b,12c could merely be operated sequentially to effect cyclical extraction and analysis at sampling points A,B,C,A,B,C,A,B,C in a sequenced mode of operation; and/or extraction and analysis may be performed at selected sampling point A for longer periods of time than is performed at sampling points B or C.

Each gas conduit assembly 14a, 14b,14c is shown as including, in addition to the extraction probes 18a,18b,18c, a sample gas supply conduit 34 and a purging gas return line 36. FIG. 2 illustrates best the extraction probe 18 used in each gas conduit assembly 14a,14b,14c shown in FIG. 1B. Preferably, the probe 18 is an elongated hollow tubular water cooled probe having open end 37 provided for positioning inside the fume duct 16 at the desired sampling point in the exhaust gas flow 100. To minimize the delay time associated with extracting the off-gas sample through the probe 18, the probe 18 incorporates a coaxially located smaller diameter extraction line 38. As shown best in FIG. 2, the end of the extraction line 38 extends downwardly along the probe interior, to be in close proximity to the end opening 37 of the main larger diameter body of the probe 18. By using the extended smaller diameter extraction line 38, the residence time for off-gas sample extracted through the probe 18 is markedly reduced. The end of the extraction line 38 may also incorporate a suitably designed primary filter, to reduce any fume dust infiltration therein. The extraction line 38 is preferably cleaned by periodically back purging, as for example, by selectively supplying a pressurized nitrogen gas or reverse airflow through the extraction line 38 from a suitable pressurized source or pump assembly 64 (FIG. 4), via the gas return conduit 36 to dislodge and remove particulate matter accumulated thereon.

In an alternate construction, the gas return conduit 36 may be provided to exhaust analyzed sample gas back into the fume duct 16, and/or provide the pressurized purging gas flow along the interior of the probe 18, to facilitate cleaning and the dislodging of any dust or debris accumulating along the outside of the extraction line 38.

FIG. 2 illustrates the extraction line 38 of each probe 18 as being fluidically coupled to the gas supply conduit 34, used to convey extracted off-gas samples from each sampling point A,B,C to the associated gas sampling analyzer 12a,12b,12c. The gas supply conduit 34 is shown as fluidically coupled to the upper outer end of the probe extraction line 38 to receive the extracted gas sample therefrom. The supply conduit 34 is provided with a resistance coil heater strip or other suitable heating jacket 40 and surrounding thermal insulation 41. The heater strip 40 is operable to maintain the extracted gas sample at a temperature of between about 80° C. and 160° C., and more preferably 100° C. to 130° C.±10° C. as the sample moves along the gas supply conduit 34 between the probe 18 and to the associated gas sampling analyzer 12.

Figure 3:
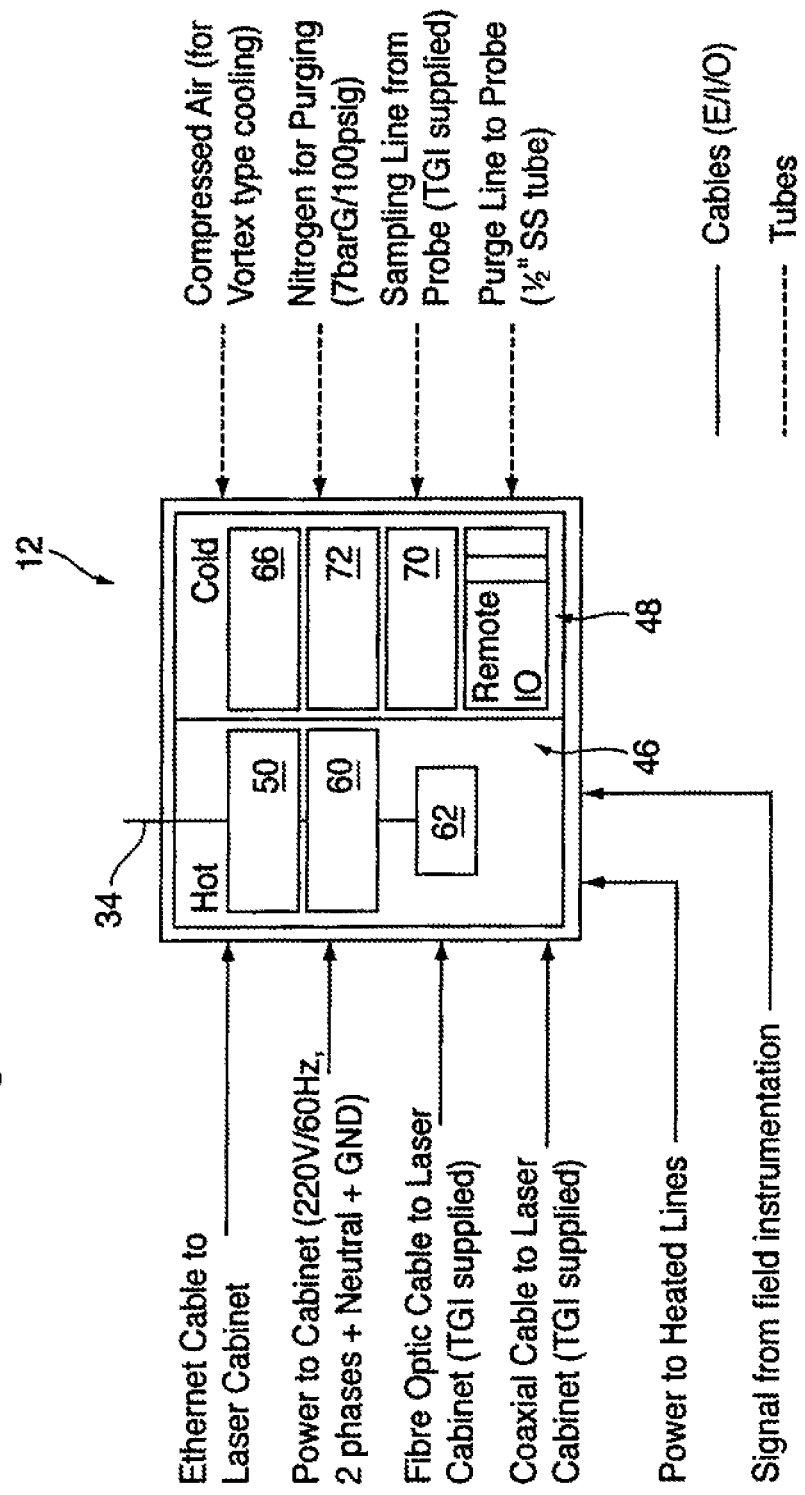
FIG. 3 illustrates schematically a gas sampling analyzer used in the gas analysis and control system shown in the partial views of FIGS. 1A and 1B.
Figure 4:
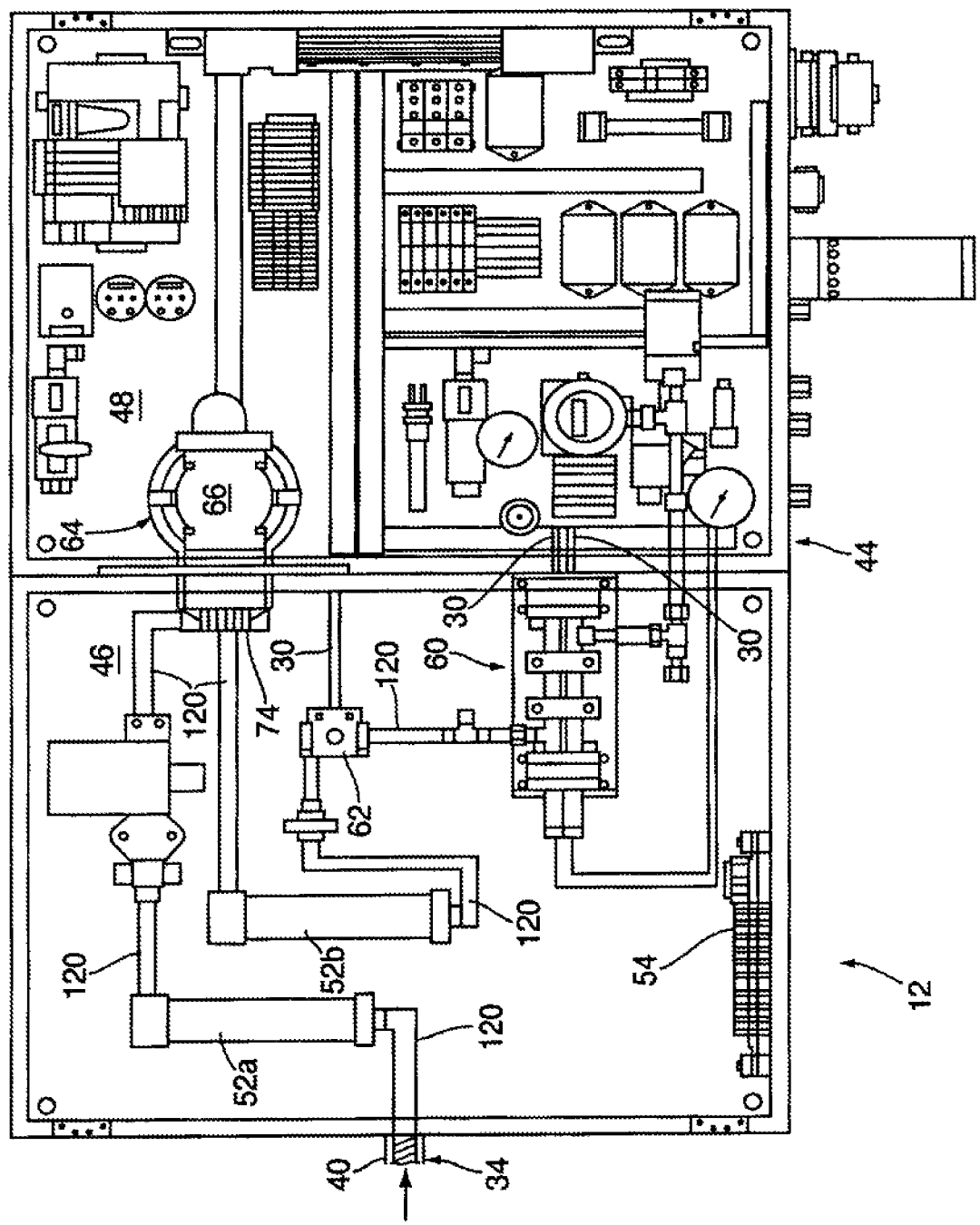
FIG. 4 illustrates schematically an interior view of the gas sampling analyzer shown in FIG. 3, illustrating gas water vapour and gas component measuring cells and a gas filter assembly in accordance with a preferred embodiment.

FIGS. 3 and 4 show best each gas sampling analyzer 12 used in the system 10 in accordance with a preferred embodiment of the invention. The sampling analyzer 12 is provided with an exterior metal cabinet 44 which is divided internally into heated and cooled or cold sections 46,48. The cabinet 44 is provided with an overall compact design having width and height dimensions of between about 0.5 to 1.25 metres, and a cabinet depth of about 0.15 to 0.4 metres. The compact size of the gas analyzer 12 advantageously allows its placement in closer proximity to the fume duct 16, and without the requirement that it be housed with a dedicated or special room or enclosure. As a result, the gas sampling analyzers 12a,12b,12c may be provided in close proximity to, and preferably within 1 to 20 metres, and most preferably within 5 to 15 metres of the associated sampling point A,B,C, with a corresponding shorter length of gas sampling conduit 34 being used to communicate with each probe 18a, 18b,18c.

As illustrated schematically in FIG. 3, the heated section 46 of the cabinet 44 is used to house a gas filter assembly 50, a gas component optical measuring cell 60 used to detect and measure selected target gas components in the extracted off-gas sample, and a water detection cell 52 for detecting water vapour content in the extracted gas.

An induction coil heater 54 (FIG. 4) is disposed within the heated section 46 of the cabinet 44. The heater 54 is operable to heat the heated section 46 to a temperature above the condensation point of water vapour in the extracted off-gas sample, preferably to a temperature between about 80° C. and 160° C., and more preferably from about 100° C. to about 130° C.±10° C. As will be described, preferably, the gas component measuring cell 60 is operable to measure the concentration of CO, $CO_2$, $O_2$ and/or $H_2$ as individual components of the extracted off-gas sample. FIG. 3 illustrates schematically the cold section 48 of the cabinet 44 as housing the pump motor 66 of the gas analyzer pump assembly 64 (FIG. 4), as well as general cooling and purging valves, temperature sensors 70 and the gas analyzer electronics 72 which may be more susceptible to temperature damage.

FIG. 4 illustrates best the pump assembly 64 as further having a pump head 74 which is mechanically operable by way of the pump motor 66. The pump head 74 is positioned within the heated section 46 of the cabinet 44. It is to be appreciated that by maintaining the pump motor 66 in the cooled section 48, the risk of pump overheating and damage may be minimized.

FIG. 4 illustrates the heated gas supply conduit 34 as fluidically communicating with internal cabinet gas supply conduit 120 disposed within the cabinet heated section 46, and which is fluidically coupled to the pump head 74. Because the heated section 46 is maintained at a desired heated temperature by the induction coil heater 54, separate heating for the gas supply conduit 120 as it extends through the cabinet 44 is not required.

The filter assembly 50 includes an upstream coarse particulate filter 52a and a downstream fine particulate filter 52b. The gas supply conduit 120 is provided to convey the extracted gas sample initially through to the measuring cell 60 after it passages through the coarse filter 52a, pump head 74 and the fine filter 52b. The applicant has appreciated that by providing the pump head 74 upstream from the fine filter 52a and in a position downstream from the coarse filter 52a, the extracted gas sample is advantageously introduced into the fine filter 52b under a positive pressure. FIG. 4 further illustrates the conduit 120 as fluidically communicating with both the measuring cell 60 and water vapour sensor 62 for detecting sample water vapour content upstream thereof. It is to be appreciated, that in an alternate embodiment, the optical measuring cell 60 could be positioned upstream from the water vapour sensor 62, and/or the water vapour sensor 62 could be omitted from the gas analyzer 12 in its entirety.

As a result, the activation of the pump assembly 64 is used to extract and draw off-gas samples through the probe 18 and along the heated gas supply tube 34 into the cabinet 44. As the gas sample moves into the cabinet 44 it moves via conduit 120 through the filters 52a,52b, and then into the water vapour sensor 62 and optical measuring cell 60.

Figure 5:
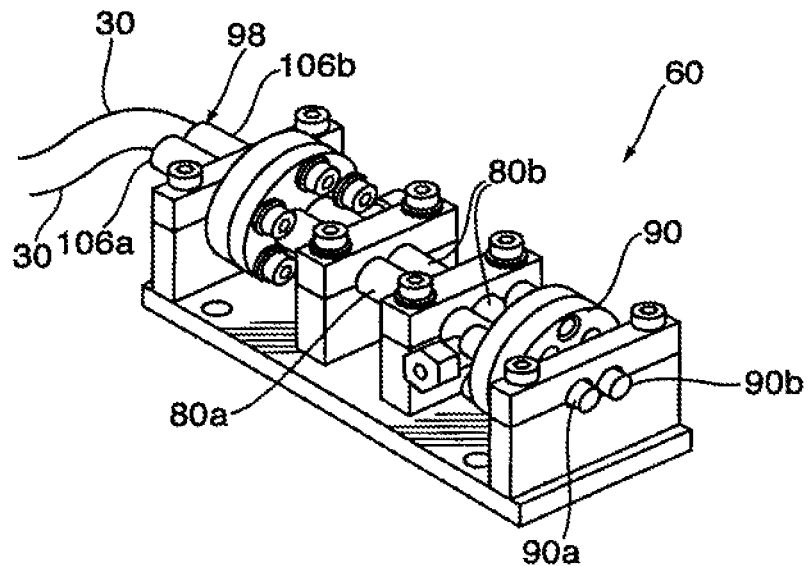
FIG. 5 shows an enlarged perspective view of the gas component measuring cell shown in FIG. 4.
Figure 6:
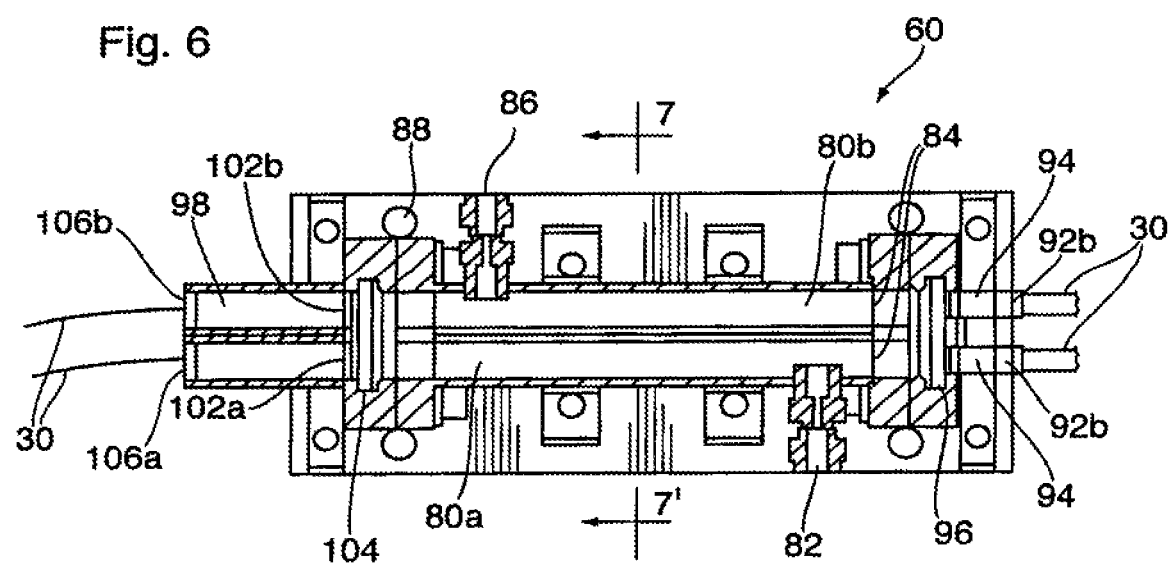
FIG. 6 illustrates schematically the gas component measuring cell shown in FIG. 5.
Figure 7:
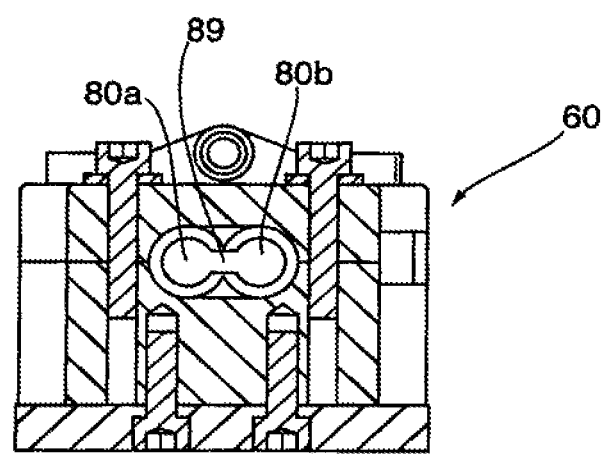
FIG. 7 shows a cross-sectional view of the gas component measuring cell illustrated in FIG. 6 taken along line 7-7'.

FIGS. 5 to 7 illustrate best the gas component measuring cell 60 used in the gas sampling analyzer 12 shown in FIG. 4. Most preferably, the measuring cell 60 is provided as a modular unit which is adapted for simplified replacement and removal. The measuring cell 60 is shown best in FIGS. 6 and 7 as including two elongated and parallel arranged cylindrical sampling chambers 80a,80b. Each of the sampling chambers 80a,80b extend along parallel longitudinal axis from adjacent first ends 84 to respective second ends 88 spaced therefrom. As shown best in FIG. 7, the sampling chambers 80a,80b are open to each other by a narrow slit opening 89 extending along their proximate longitudinal adjacent edges, and which has a width selected to allow substantially unrestricted gas flow therebetween, whilst substantially preventing the movement of light energy from the sampling chamber 80a into chamber 80b and vice versa.

FIG. 6 illustrates the measuring cell 60 as further including a gas inlet port 82 open to the sampling chamber 80a adjacent to its first end 84, with a gas outlet port 86 open to sampling chamber 80b adjacent to its second opposed end 88. The lengths of each of the sampling chambers 80a,80b is correlated to an absorption profile of the desired target gas component to be analyzed by the measuring cell 60. Further, by its modular nature, each cell 60 may be readily replaced and the analyzer 12 modified to detect different gas components by selecting sampling chambers 80a,80b having the desired target gas absorption profiles.

FIG. 5 illustrates the measuring cell 60 as including an optical head 90 positioned towards the first ends 84 of the chambers 80a,80b. The optical head 90 is provided with a pair of optical emitters 92a,92b each respectively coaxially aligned with the sample chamber 80a,80b longitudinal axis. Most preferably each of the emitters are provided with a collimator. The optical emitters 92a,92b are optically connected by way of the fibre optical cabling of the fiber optic/coaxial cables 30 to the tunable diode lasers 24a,24b by way of the switching unit 26. Each optical emitter 92a,92b further includes a collimator 94, adapted to broaden the width of the laser beam emitted therefrom, so as to minimize any potential interference by dust or particles which may be entrained in the extracted off-gas sample. In this manner the coherent light beam from the lasers 24a,24b is emitted from each respective emitter 92a,92b as a collimated laser beam, thereby reducing the potential that remaining entrained dust or particulate matter is the gas sample could result in false readings.

Preferably, a removable window or lens 96 is positioned at the first ends 84 of the chambers 80a,80b. When positioned, the window 96 substantially seals the first ends 84 of the sampling chambers 80a,80b preventing the movement of sampled gas and/or any entrained dust therepast. A removable window or lens 104 further is provided at the second end 88 of the sampling chambers 80a,80b to seal the sampling chamber second ends 88. The removal of the windows 96,104 advantageously allows for simplified cell maintenance and periodic cleaning.

FIG. 6 further illustrates the measuring cell 60 as having a detector assembly 98 positioned toward the second end 88 of the sampling chambers 80a,80b. The detector assembly 98 includes a pair focusing lenses 102a,102b and optical detectors 106a,106b positioned towards the second ends 88 of each respective sampling chamber 80a,80b. The optical sensor 106a,106b are provided in electronic communication with the CPU 20 by way of coaxial wiring of the fiber optic/coaxial cable 30. The focusing lenses 102a,102b are selected to refocus the collimated laser beams towards each respective detector 106a,106b with the light energy collected thereby converted to electronic data signals.

For water vapour analysis, the extracted gas sample is passed through the water vapour sensor 62 prior to analysis in the measuring cell 60. In one non-limiting construction, the sensor 62 may be an optically based sensor constructed in a manner similar to measuring cell 60. In such a construction, the sensor 62 may be provided for selective optical coupling to laser 24c by way of fiber optic cabling of fiber optic/coaxial cable 30. Most preferably the water vapour sensor 62 is provided with a coherent light source emitter which is optically coupled to the laser 24c, and detector. The sensor 62 is provided with an optical length which corresponds to an absorption profile for water vapour in the selected gas sample.

In use of the gas analysis and control system 10, the CPU 20 is used to activate the selected gas sampling analyzer 12a,12b,12c to extract and analyze an off-gas sample at the desired extraction point A,B,C of interest. Signals from the CPU 20 are received by the selected analyzer electronics 72, and used to activate its pump motor 66. As the motor 66 is activated, the off-gas sample is substantially continuously drawn from the fume duct 16 and along the gas supply conduits 34 via associated extraction probe 18 into the heated section 46 of the cabinet 44. Most preferably, the pump motor 66 is selected to convey the extracted gas sample along the supply conduit 34 and through the filter 52a and measuring cell 60 at higher flow rates, as for example of up to about 40 litres per minute, to minimize residence time and analytical response delays. As the extracted gas sample moves through the cabinet 44, it passes via conduit 120 through the coarse filter 52a. The off-gas sample is then forced under positive pressure through the fine filter 52b, and into the water sensor 62 for water content analysis. On moving from the water sensor 62, the off-gas sample moves and via the gas inlet port 82, into the sampling chambers 80a,80b of the measuring cell 60.

Concurrently, the control unit 20 is used to emit coherent light beams from the lasers 24a,24b,24c from the optical emitters 92a,92b of the measuring cell 60 as well as from an emitter within the water vapour sensor 62, for detection by the associated detectors.

In the optical measuring cell 60, each sampling chamber 80a,80b is provided with a longitudinal length which is correlated to an absorption profile of the specific target gas component which is to be analyzed. In a most preferred construction, the sample chambers 80a,80b are provided with lengths correlating to absorption profiles selected for analyzing respectively CO and $CO_2$, and $O_2$ concentrations in the extracted off-gas sample. The coherent light beams emitted by the optical emitters 92a,92b are focused and are detected by the optical detectors 106a,106b respectively. The detector and analyzer electronics 72 convert the detected light energy to electronic data signals, which are thereafter transmitted by way of the coaxial cabling of fiber optic/coaxial cables 30 back to the CPU 20. Depending upon the concentration and/or change of selected target components in the sampled off-gas, the control unit 20 may thereafter output control signals to the furnace plant to regulate or vary overall furnace operations.

It is to be appreciated, in a preferred construction a single laser may thus be used to effect both CO and $CO_2$ analysis. In an alternate embodiment, separate sample chambers 80 could however be provided to individually analyze CO and $CO_2$ and which could be optically coupled to separate or a common coherent light source.

In the preferred embodiment, the gas analyzer cell 60 is also designed to operate at temperatures above the off-gas dew point and/or condensation point of vapour and/or validate phase gas components. This advantageously avoids the need for an additional off-gas condensation step, and the need for a condenser, allowing for a further reduction in the physical size of the sampling station. In addition, by analyzing wet off-gas and optimizing the design of each specific analytical cell and using suitable software in the signal analysis unit, the current invention also enables full spectrum analysis of a variety of different types of gases including, without restrictions $H_2O$ vapor, CO, $O_2$, $CO_2$ and $H_2$. In many metallurgical and combustion applications, having such a full spectrum analysis enables the concentration $N_2$ to be determined by difference from 100%.

Following analysis, the analyzed gas sample is then vented either into the atmosphere, or optionally, vented back into the fume duct 16 by way of the gas return conduit 36. While the use of a gas return conduit 36 to return sampled gas to the fume duct 16 may represent one embodiment of the invention, the invention is not so limited. In alternate configuration, the gas return conduit 36 may be used to convey purging nitrogen gas to the extraction probe 18 to assist in probe cleaning. Valving within the cooled section 48 of the cabinet 44 may be provided to control and facilitate purging operations.

The current invention also enables a simplified and effective arrangement for analyzing off-gas compositions at multiple sample points A,B,C by connecting a compact sampling analyzer 12 at each sampling point by fiber optic/coaxial cables 30 to common lasers 24 and a single CPU 20 or signal analyzing unit equipped to distribute the optical signals between the respective sampling stations 12.

While the detailed description describes the apparatus 10 as including tunable diode lasers 24a,24b,24c, which are operable in the mid-IR range it is to be appreciated that other lasers and/or optical analyzers may also be used. Other types of lasers which could be selected include those which are operable in the near-IR and visible wavelength range. Similarly whilst the aforementioned description describes the system 10 as being used in the analysis of dusty industrial steel plant furnace off-gases, it is to be appreciated that the current system and method has application across a variety of different types of exhaust systems. These include other types of industrial furnaces, as well as coal and power generated off-gas flue streams and the like.

Although the detailed description describes the control system 10 as including three sampling cabinets 12a,12b,12c, it is to be appreciated that the system 10 may be installed with fewer or greater number of sampling cabinets 12 without departing from the present invention. Similarly, while the invention shown in FIGS. 1A and 1B illustrate the system 10 as including a gas extraction probe 18a,18b,18e associated with each gas sampling cabinet 12a,12b,12c, in an alternate configuration, the number of extraction probes 18 could be provided for selective fluid communication with a single sampling cabinet 12 with a view to minimizing system hardware costs.

While the detailed description describes each sampling analyzer 12 as having a single measuring cell 60 which includes two parallel sampling chambers 80a,80b, the invention is not so limited. It is to be appreciated that the gas sampling analyzers 12 may include multiple measuring cells 60, each with fewer or greater numbers of sampling chambers 80 provided for optical and electric coupling to associated coherent light source emitters and detectors. Similarly, while the preferred measuring cell 60 is described as having generally cylindrical sampling chambers 80 which fluidically communicate by way of a longitudinal slit opening, the invention is not restricted specifically to the best mode which is described. Sampling chambers having differing lengths and/or profiles may also be used and will now become apparent.

The system 10 is described with reference to FIGS. 1A and 1B whereby separate lasers 24a,24b are used to emit coherent light beams along a respective sample chamber 80a,80b for CO, $CO_2$ and $O_2$ analysis. In an alternate construction, a single laser source could be provided to measure each of CO, $CO_2$ and $O_2$ with output beam energy either split between sampling chambers 80a,80b by a suitable optical splitter (not shown), or switched therebetween by a multiplexer 28 and/or switching unit 26.

Although the detailed description describes and illustrates various preferred embodiments, the invention is not restricted to the specific constructions which are described. Many variations and modifications will now occur to persons skilled in the art. For a definition of the invention, reference may now be had to the appended claims.

We claim:

1. A system for measuring gas components of an industrial furnace off-gas stream,
the system comprising,
a coherent light source comprising a plurality of tunable lasers operable to output an associated coherent light beam,
a plurality of off-gas analyser apparatus, each off-gas apparatus including,
a cabinet having a heated compartment,
a gas component measuring cell comprising first and second elongated sampling chambers, said sampling chambers being disposed within said heated compartment and extending from a respective first end to a second end spaced therefrom, each of the sampling chambers having a respective length correlated to an absorption profile of an associated target gas component of said off-gas stream, the sampling chambers being in fluid communication with an associated analyser gas inlet,
an optical head adapted for selective optical coupling to said coherent light source, the optical head including a plurality of emitters each respectively positioned towards the first end of an associated said sampling chamber for emitting a respective said coherent light beam therealong, and
a detector assembly comprising a plurality of detectors each respectively positioned towards the second end of an associated said sampling chamber for receiving said coherent light beam emitted therealong,
a gas supply conduit providing fluid communication between a first portion of said furnace off-gas stream and the associated gas inlet of a first said off-gas analyser apparatus to fluidically communicate a first extracted gas sample thereto, and between a second portion of said furnace off-gas stream downstream from said first portion and the associated gas inlet of a second said off-gas analyser apparatus to fluidically communicate a second extracted gas sample thereto, and
a switching assembly operable to selectively optically couple said coherent light source to the optical head of a selected said off-gas analyser apparatus depending on the portion of the furnace off-gas stream form which analysis of the gas samples is desired.

2. The system as claimed in claim 1, wherein said measuring cell comprises an elongate opening selected to allow a substantially unrestricted flow of the communicated extracted gas sample between the first sampling chamber and the second sampling chamber substantially along their longitudinal length.

3. The system as claimed in claim 1, wherein each off-gas analyser apparatus further includes:
   a water detection cell in fluid communication with the gas component measuring cell, the water detection cell operable to detect a water vapour content of the extracted gas sample, and
   a heater for maintaining a temperature of the heated compartment above the condensation point of water vapour in the extracted gas sample.

4. The system as claimed in claim 3, wherein each off-gas analyser apparatus includes an associated pump assembly, wherein the system includes a pump assembly operated to extract said gas sample from said off-gas stream, and convey the extracted gas sample to the gas component measure cell as a substantially continuous sample flow.

5. The system as claimed in claim 4, further include a filter assembly for filtering particulates from the continuous sample flow in an upstream position from the off-gas analyser apparatus, the filter assembly being disposed in the heated compartment.

6. The system as claimed in claim 5, wherein sample flow having a flow rate selected at 10 to 40 litres per minute.

7. The system as claimed in claim 6, wherein the cabinet includes a non-heated compartment, the pump assembly including a motor housed substantially within an interior of the non-heated compartment.

8. The system as claimed in claim 5, wherein sample flow having a flow rate selected at 10 to 40 litres per minute.

9. The system as claimed in claim 4, wherein the switching assembly is selected from the group consisting of a multiplexer/de-multiplexer and an optical splitter, and said target gas components comprise at least two of CO, $CO_2$ and $H_2O$.

10. The system as claimed in claim 1, wherein each said emitter further comprises a collimator selected to emit said coherent light beam as a collimated light beam along said associated sampling chamber, and
   each said detector comprises a lens configured to refocus the collimated light beam towards an associated optical detector.

11. The system as claimed in claim 1, wherein the switching assembly is selected from the group consisting of a multiplexer/de-multiplexer and an optical splitter, and said target gas components comprise at least two of CO, $CO_2$ and $H_2O$.

12. A system for measuring gas components of an industrial furnace off-gas stream,
   the system comprising,
   a coherent light source comprising at least one tunable laser operable to output an associated coherent light beam,
   a plurality of off-gas analyser apparatus,
   a gas supply conduit providing fluid communication between a first portion of said furnace off-gas stream and a gas inlet of a first associated said off-gas analyser apparatus to fluidically communicate a first extracted gas sample thereto, and between a second portion of said furnace off-gas stream downstream from said first portion and an associated gas inlet of a second said off-gas analyser apparatus to fluidically communicate a second extracted gas sample thereto,
   wherein each off-gas apparatus comprises,
      a cabinet having a heated compartment,
      a gas component measuring cell comprising first and second sampling chambers disposed within said heated compartment, said first and second sampling chambers fluidically communicating with said analyser inlet for receiving the communicated extracted gas sample therein, the sampling chambers extending longitudinally from a respective first end to a second end spaced therefrom, each of the sampling chambers having a respective length correlated to an absorption profile of an associated target gas component of said off-gas stream, an elongate opening configured to allow the substantially unrestricted flow of the communicated extracted gas sample between the first sampling chamber and the second sampling chamber,
      an optical head adapted for selective optical coupling to said coherent light source, the optical head including a plurality of emitters, each respectively positioned towards the first end of an associated said sampling chamber for emitting a respective said coherent light beam therealong, and
      a detector assembly comprising a plurality of detectors, each respectively positioned towards the second end of an associated said sampling chamber for receiving said coherent light beam emitted therealong,
      a switching assembly operable to selectively optically communicate he output coherent light beam to the optical head of a selected said off-gas analyser apparatus depending on the portion of the furnace off-gas stream to be analysed.

13. The system as claimed in claim 12, wherein said first and second sampling chambers comprise generally adjacent coaxially parallel cylindrical chambers, said opening comprising a longitudinally extending slit opening having a width selected to substantially prevent movement of coherent light beam energy emitted from the emitter of one said sampling chamber from being received by the detector of the other said sampling chamber.

14. The system as claimed in claim 12, wherein each off-gas analyser apparatus further includes:
   a water detection cell in fluid communication with the gas component measuring cell, the water detection cell operable to detect a water vapour content of the extracted gas sample, and
   a heater for maintaining a temperature of the heated compartment above the condensation point of water vapour in the extracted gas sample.

15. The system as claimed in claim 12, wherein each off-gas analyser apparatus includes an associated pump assembly, and
   wherein the system includes a pump assembly operated to extract said gas sample from said off-gas stream, and convey the extracted gas sample to the gas component measure cell as a substantially continuous sample flow.

16. A system for measuring gas components of an industrial furnace off-gas stream,
   the system comprising,
   a coherent light source comprising at least one tunable laser operable to output an associated coherent light beam,
   at least one off-gas analyser apparatus,
   a gas supply conduit providing fluid communication between at least a first portion of said furnace off-gas stream and a gas inlet of an associated said off-gas analyser apparatus to fluidically communicate an extracted gas sample thereto, each said off-gas apparatus comprising, a gas component measuring cell comprising first and second sampling fluidically communicating with said analyser inlet for receiving the communicated extracted gas sample therein, the sampling chambers extending longitudinally from a respective first end to a second end spaced therefrom, each of the sampling chambers having a respective length correlated to an absorption profile of an associated target gas component of said communicated extracted gas sample, a longitudinally extending slit opening configured to allow the substantially unrestricted flow of the communicated extracted gas sample between the first sampling chamber and the second sampling chamber, slit opening having a width selected to substantially prevent coherent light beam energy emitted from the emitter of one said sampling chamber from being received by the detector of the other said sampling chamber, an optical head including a plurality of emitters, each respectively positioned towards the first end of an associated said sampling chamber for emitting a respective said coherent light beam therealong, and a detector assembly comprising a plurality of detectors, each respectively positioned towards the second end of an associated said sampling chamber for receiving said coherent light beam emitted therealong, the output coherent light beam being optically coupled to the optical head of a selected said off-gas analyser apparatus depending on the portion of the furnace off-gas stream to be analysed.

17. The system as claimed in claim 16, wherein each said emitter further comprises a collimator selected to emit said coherent light beam as a collimated light beam along said associated sampling chamber, and each said detector comprises a lens configured to refocus the collimated light beam towards an associated optical detector.

18. The system as claimed in claim 17, wherein the system includes a pump assembly operated to extract said gas sample from said off-gas stream, and convey the extracted gas sample to the gas component measure cell as a substantially continuous sample flow.

19. The system as claimed in claim 18, wherein the at least one off-gas analyser includes a cabinet having heated compartment and an unheated compartment, the heated compartment including:

a heating assembly operable to maintain a temperature of the extracted gas sample therein above the condensation point of water, the first and second sampling chambers being disposed in said heated compartment, and the pump assembly includes a pump motor housed substantially within an interior of the unheated compartment.

20. The system as claimed in claim 16, wherein said extracted gas sample comprises an off-gas sample from a steel making furnace off-gas stream, and said target gas components comprise at least two of $CO$, $CO_2$ and $O_2$.

* * * * *